US010196587B2

(12) United States Patent
Doi

(10) Patent No.: US 10,196,587 B2

(45) **Date of Patent: *Feb. 5, 2019**

(54) CLEANSING COMPOSITION FOR SKIN OR HAIR

(71) Applicant: KAO CORPORATION, Tokyo (JP)

(72) Inventor: Yasuhiro Doi, Kainan (JP)

(73) Assignee: KAO CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/594,154

(22) Filed: May 12, 2017

(65) Prior Publication Data

US 2017/0246096 A1 Aug. 31, 2017

Related U.S. Application Data

(63) Continuation of application No. 14/417,076, filed as application No. PCT/JP2013/076173 on Sep. 19, 2013, now Pat. No. 9,725,676.

(30) Foreign Application Priority Data

Sep. 20, 2012 (JP) ................................. 2012-207642
Jun. 25, 2013 (JP) ................................. 2013-133219

(51) Int. Cl.

| | |
|---|---|
| ***C11D 1/00*** | (2006.01) |
| ***C11D 1/14*** | (2006.01) |
| ***A61K 8/46*** | (2006.01) |
| ***A61Q 5/02*** | (2006.01) |
| ***A61Q 19/10*** | (2006.01) |
| ***C07C 309/67*** | (2006.01) |
| ***A61K 45/06*** | (2006.01) |
| ***C11D 3/00*** | (2006.01) |
| ***C11D 3/37*** | (2006.01) |
| ***C11D 3/43*** | (2006.01) |
| ***C11D 3/48*** | (2006.01) |
| ***C11D 3/50*** | (2006.01) |

(52) U.S. Cl.

CPC .............. *C11D 1/143* (2013.01); *A61K 8/466* (2013.01); *A61K 45/06* (2013.01); *A61Q 5/02* (2013.01); *A61Q 19/10* (2013.01); *C07C 309/67* (2013.01); *C11D 3/0089* (2013.01); *C11D 3/3796* (2013.01); *C11D 3/43* (2013.01); *C11D 3/48* (2013.01); *C11D 3/50* (2013.01); *A61K 2800/48* (2013.01); *A61K 2800/51* (2013.01); *A61K 2800/5426* (2013.01); *A61K 2800/596* (2013.01)

(58) Field of Classification Search

None

See application file for complete search history.

(56) References Cited

U.S. PATENT DOCUMENTS

| | | | |
|---|---|---|---|
| 3,332,878 | A | 7/1967 | Coward et al. |
| 3,708,437 | A | 1/1973 | Sweeney |
| 3,808,157 | A | 4/1974 | Dewitt et al. |
| 4,028,283 | A | 6/1977 | Murata et al. |
| 4,075,129 | A | 2/1978 | Murata et al. |
| 4,220,548 | A | 9/1980 | Hashimoto et al. |
| 4,507,223 | A | 3/1985 | Tano et al. |
| 4,555,351 | A | 11/1985 | Morita et al. |
| 4,589,988 | A | 5/1986 | Rieck et al. |
| 4,597,879 | A | 7/1986 | Morita et al. |
| 4,715,991 | A | 12/1987 | Hirakouchi et al. |
| 4,852,653 | A | 8/1989 | Borchardt |
| 4,925,976 | A | 5/1990 | Terao et al. |
| 5,078,916 | A | 1/1992 | Kok et al. |
| 5,580,494 | A | 12/1996 | Sandhu et al. |
| 5,876,705 | A | 3/1999 | Uchiyama et al. |
| 6,156,297 | A | 12/2000 | Maurin et al. |
| 6,184,190 | B1 | 2/2001 | D'Ambrogio et al. |
| 6,403,654 | B1 | 6/2002 | De Oliveira |
| 6,586,379 | B1 | 7/2003 | Seipel |
| 6,656,454 | B1 | 12/2003 | Koester et al. |
| 2002/0146442 | A1 | 10/2002 | Sendelbach et al. |
| 2007/0031362 | A1 | 2/2007 | Kreeger et al. |
| 2011/0039744 | A1 | 2/2011 | Heath et al. |
| 2012/0058067 | A1 | 3/2012 | Van Gogh et al. |
| 2012/0270764 | A1 | 10/2012 | Brown et al. |
| 2013/0252855 | A1 | 9/2013 | Weerasooriya et al. |
| 2014/0079658 | A1 | 3/2014 | Terazaki et al. |

(Continued)

FOREIGN PATENT DOCUMENTS

| | | | |
|---|---|---|---|
| CA | 1338239 | C | 4/1996 |
| CN | 86 1 02800 | A | 1/1987 |
| EP | 0 377 261 | A2 | 7/1990 |

(Continued)

OTHER PUBLICATIONS

International Search Report and Written Opinion of the International Searching Authority dated Mar. 20, 2013, for International Application No. PCT/JP2013/076176.

International Search Report and Written Opinion of the International Searching Authority dated Mar. 20, 2014, for International Application No. PCT/JP2013/076171.

International Search Report and Written Opinion of the International Searching Authority dated Mar. 20, 2014, for International Application No. PCT/JP2013/076172.

(Continued)

*Primary Examiner* — Necholus Ogden, Jr.

(74) *Attorney, Agent, or Firm* — Birch, Stewart, Kolasch & Birch, LLP

(57) ABSTRACT

The present invention provides a cleansing composition for skin or hair which can provide a good durability of foam and rinse feel, give good combability and softness from during rinsing to after drying while imparting manageability to hair when the cleansing composition is applied to hair, and give good moist feeling to skin when the cleansing composition is applied to skin.

The cleansing composition for skin or hair is a cleansing composition comprising an internal olefin sulfonate (A) having 12 or more and 24 or less carbon atoms.

16 Claims, No Drawings

(56) References Cited

U.S. PATENT DOCUMENTS

| | | | |
|---|---|---|---|
| 2014/0080747 A1 | 3/2014 | Hirahara et al. |
| 2015/0202134 A1 | 7/2015 | Yoshikawa et al. |

FOREIGN PATENT DOCUMENTS

| | | | |
|---|---|---|---|
| EP | 0351928 | B1 | 6/1993 |
| JP | 49-78706 | | 7/1974 |
| JP | 54-134711 | A | 10/1979 |
| JP | 55-43138 | A | 3/1980 |
| JP | 55-56196 | A | 4/1980 |
| JP | 56-167799 | A | 12/1981 |
| JP | 59-27995 | A | 2/1984 |
| JP | 59-222466 | A | 12/1984 |
| JP | 61-134366 | A | 6/1986 |
| JP | 61-45964 | B2 | 10/1986 |
| JP | 1-151510 | A | 6/1989 |
| JP | 1-272564 | A | 10/1989 |
| JP | 2003-81935 | A | 3/2003 |
| JP | 2003-183152 | A | 7/2003 |
| JP | 2006-527785 | A | 12/2006 |
| JP | 2007-15940 | A | 1/2007 |
| JP | 2009-256211 | A | 11/2009 |

OTHER PUBLICATIONS

International Search Report and Written Opinion of the International Searching Authority dated Mar. 20, 2014, for International Application No. PCT/JP2013/076173.

International Search Report and Written Opinion of the International Searching Authority dated Mar. 20, 2014, for International Application No. PCT/JP2013/076174.

Kosswig et al., "Surfactants", Wiley-VCH Verlag GmbH & Co. KGaA, Weinheim, 2005, XP002554753, pp. 1-76.

Kao Corporation, "Kao Akypo RLM-45NV", Product Specification for Sodium Laureth-6 Carboxylate, retrieved online on Dec. 6, 2016, 1 page.

U.S. Office Action dated Jan. 25, 2016, for U.S. Appl. No. 14/417,079.

Wikihow, "How to Shampoo and Condition Your Hair," https://web.archive.org/web/20090418054258/http://www/wikihow.com/Shampoo-and-C . . . , Apr. 18, 2009, 2 pages.

CLEANSING COMPOSITION FOR SKIN OR HAIR

CROSS-REFERENCE TO RELATED APPLICATIONS

This application is a Continuation of application Ser. No. 14/417,076 filed on Jan. 23, 2015, which is a National Phase of PCT International Application No. PCT/JP2013/076173 filed on Sep. 19, 2013, which claims priority under 35 U.S.C. § 119(a) to Patent Application No. 2012-207642 filed in Japan on Sep. 20, 2012 and Patent Application No. 2013-133219 filed in Japan on Jun. 25, 2013. All of the above applications are hereby expressly incorporated by reference into the present application.

FIELD OF THE INVENTION

The present invention relates to a cleansing composition for skin or hair such as a shampoo and a body shampoo.

BACKGROUND OF THE INVENTION

A cleansing agent is required to have a variety of functions such as emulsifying or cleaning the components of dirt and stains such as oil. Especially, unlike an industrial cleaner, a laundry cleaner, and a house cleaner, it is considered important that a cleansing agent used for skin or hair has not only detergency, excellent foaming performance and creamy foam quality for easy wash, but also a good durability of foam, a favorable rinsability and a good feel after rinsing and drying. Particularly in the case of hair, sliding property, good finger combability and softness of the hair from during rinsing to after drying are desired, and in the case of skin, such an impression is desired that freshness after towel drying and a moist feeling after drying is imparted to the skin washed with a cleansing agent.

Under the foregoing circumstances, olefin sulfonate, which is one of the anionic surfactants, is generally obtained by sulfonating olefin through reactions with a gaseous sulfur trioxide-containing gas, followed by neutralization and then hydrolysis of the resulting sulfonic acid. Olefin sulfonate is used in various cleansing agents.

For example, Patent Document 1 discloses a cleansing composition containing a specific internal olefin sulfonate for the purposes of increasing the solubilizing ability, penetrating ability, and interfacial tension reducing ability, and describes that when the above cleansing composition is used as a shampoo, it lathers well without friction, and achieves an improved feel. Also, Patent Document 2 discloses a cleansing composition containing a specific internal olefin sulfonate for the purposes of improving detergency, and describes examples of application to shampoos and the like, and Patent Document 3 also describes a water-soluble liquid cleansing agent containing a specific internal olefin sulfonate and having a low cloud point.

Meanwhile, Patent Document 4 discloses a cleansing composition containing an olefin sulfonate and a low viscous hydrophobic silicone oil such as octamethyltetrasiloxane and decamethylpentasiloxane to improve smoothness and silky touch of hair after drying.

CITATION LIST

Patent Document

[Patent Document 1] JP-A-2003-81935
[Patent Document 2] U.S. Pat. No. 5,078,916
[Patent Document 3] U.S. Pat. No. 3,708,437
[Patent Document 4] JP-A-01-151510

SUMMARY OF THE INVENTION

The present invention provides a cleansing composition for skin or hair, comprising an internal olefin sulfonate (A) having 12 or more and 24 or less carbon atoms (hereinbelow, may also be referred to as "the cleansing composition of the present invention").

DETAILED DESCRIPTION OF THE INVENTION

Therefore, the present invention provides a cleansing composition for skin or hair which can provide a good durability of foam, rinse feel, give good combability, softness and manageability from during rinsing to after drying when the cleansing composition is applied to hair, and give good moist feeling to skin when the cleansing composition is applied to skin.

In light of the above, the present inventors carried out various studies. As a result, they found that a cleansing composition which can impart good combability, softness from during rinsing to after drying and manageability after drying to hair, and a sufficient moist feeling also to skin after application, while exhibiting an excellent durability of foam and rinse feel as a cleansing agent for skin or a cleansing composition for hair can be obtained by using an internal olefin sulfonate having specific number of carbon atoms.

According to the present invention, it can not only bring about a good durability of foam and rinse feel, but also, when applied to hair, impart good combability and softness from during rinsing to after drying and impart manageability to hair after drying, and, when applied to skin, impart a good moist feeling to skin.

Hereinbelow, the present invention will be described in detail.

The cleansing composition of the present invention contains an internal olefin sulfonate (A) having 12 or more and 24 or less carbon atoms.

The reason is not clear why the cleansing composition according to the present invention provides a good durability of foam and rinse feel, and gives good combability and softness from during rinsing to after drying when the cleansing composition is applied to hair, and a good moist feeling to skin when the cleansing composition is applied to skin. It is presumed that the internal olefin sulfonate having 12 or more and 24 or less carbon atoms has proper hydrophobicity, and therefore bubbles are easily broken in a diluted region by rinsing, and washed off, while part of the internal olefin sulfonate is adsorbed on skin or hair to give good combability, softness and manageability, and to improve a moist feeling to skin.

<Internal Olefin Sulfonate (A)>

From the viewpoint of improving detergency, foam quality, and foamability, and a good rinse feel and durability of foam, and also, imparting to hair good combability and softness from during rinsing to after drying and manageability after drying and a moist feeling to skin, the cleansing composition of the present invention contains an internal olefin sulfonate having 12 or more and 24 or less carbon atoms (hereinbelow, may also be referred to as a component (A)).

In the present invention, an internal olefin sulfonate is an olefin sulfonate obtained by sulfonating an internal olefin (an olefin having a double bond inside the olefin chain) as the raw material, followed by neutralization and then hydrolysis. It should be noted that the above internal olefin may also have a broad meaning including a trace amount of so-called α-olefin, in which a double bond is present at the C-1 position of the carbon chain. That is, sulfonation of an internal olefin quantitatively produces β-sultone, some of which are converted into γ-sultone and olefin sulfonic acid, which are further converted into hydroxyalkane sulfonate and olefin sulfonate in the process of neutralization and hydrolysis (for example, J. Am. Oil Chem. Soc. 69, 39 (1992)). Here, the hydroxyl group of the hydroxyalkane sulfonate thus obtained is present inside the alkane chain, and the double bond of the olefin sulfonate is present inside the olefin chain. Also, the product thus obtained is mainly a mixture of the aforementioned substances, which may partially contain a trace amount of hydroxyalkane sulfonate having a hydroxyl group at the end of the carbon chain or olefin sulfonate having a double bond at the end of the carbon chain. In the present specification, each of these products and a mixture thereof are collectively referred to as internal olefin sulfonate (component (A)), and each of the product is individually referred to as internal olefin sulfonate. It should be noted that hydroxyalkane sulfonate is referred to as the hydroxy form of an internal olefin sulfonate (hereinbelow, may also be referred to as HAS), and olefin sulfonate is referred to as the olefin form of an internal olefin sulfonate (hereinbelow, may also be referred to as IOS).

From the viewpoint of improving a durability of foam and rinse feel, imparting good combability after rinsing and manageability after drying to hair, and imparting a moist feeling to skin, the number of carbon atoms in the internal olefin sulfonate of the component (A) is 12 or more, preferably 14 or more, and more preferably 16 or more. Also, from the viewpoint of softness of the hair during rinsing, manageability after drying, and a moist feeling on the skin, the number of carbon atoms in the internal olefin sulfonate of the component (A) is 24 or less, preferably 20 or less, and more preferably 18 or less. Also, from the above points, the number of carbon atoms in the internal olefin sulfonate of the component (A) is 12 or more and 24 or less, preferably 14 or more and 20 or less, and more preferably 16 or more and 18 or less. These hydroxy form and olefin form containing various numbers of carbon atoms are derived from an internal olefin to be used as the raw material, and a hydroxy form and an olefin form containing different numbers of carbon atoms from those described above may also be contained.

From the viewpoint of improving detergency, foam quality, foamability, durability of foam and rinse feel, imparting to hair combability and softness from during rinsing to after drying and manageability after drying, and imparting a moist feeling to skin, the mass content ratio of an internal olefin sulfonate having 16 carbon atoms to an internal olefin sulfonate having 18 carbon atoms (internal olefin sulfonate having 16 carbon atoms/internal olefin sulfonate having 18 carbon atoms) in the component (A) or the cleansing composition is preferably from 50/50 to 99/1, more preferably from 60/40 to 95/5, more preferably from 70/30 to 90/10, more preferably from 75/25 to 90/10, more preferably from 75/25 to 85/15 and even more preferably from 78/22 to 85/15.

It is to be noted that the aforementioned mass ratio may be measured by a high-performance liquid chromatograph-mass spectrometer (hereinbelow, abbreviated as HPLC-MS).

Specifically, an internal olefin sulfonate having 16 carbon atoms and an internal olefin sulfonate having 18 carbon atoms are separated from the component (A) or the produced cleansing composition by HPLC, each of which may then be identified by analysis with MS, and from the HPLC-MS peak area of each internal olefin sulfonate, the mass ratio between them may be obtained.

From the viewpoint of improving detergency, foam quality, foamability, a rinse feel and durability of foam, and imparting to hair good combability and softness after rinsing, manageability after drying, and imparting a moist feeling to skin, the total content of an internal olefin sulfonate having carbon atoms and an internal olefin sulfonate having 18 carbon atoms in the component (A) is preferably 50% by mass or more, more preferably 60% by mass or more, more preferably 70% by mass or more, more preferably 80% by mass or more, more preferably 90% by mass or more, and even more preferably 95% by mass or more. It should be noted that the upper limit of the aforementioned total content is 100% by mass.

As is apparent from the aforementioned production method, the sulfonate group of the internal olefin sulfonate of the component (A) is present in the carbon chain of an internal olefin sulfonate, namely inside the olefin chain or alkane chain, and the component (A) may partially contain a trace amount of an internal olefin sulfonate having a sulfonate group at the end of the carbon chain. In the present invention, from the viewpoint of foamability, it is preferable that the content of an internal olefin sulfonate in which the sulfonate group is present at the C-2 position of the carbon chain is low, while the content of an internal olefin sulfonate in which the sulfonate group is present further inside is high in the component (A). It should be noted that when the component (A) contains an internal olefin sulfonate having 16 carbon atoms and an internal olefin sulfonate having 18 carbon atoms, it is more preferable that the content of an internal olefin sulfonate in which the sulfonate group is present at the C-2 position of the carbon chain is low, with respect to both of the above internal olefin sulfonates having 16 and 18 carbon atoms.

From the viewpoint of improving lathering property, foam quality, and a rinse feel as well as imparting good combability and softness after rinsing and manageability after drying to hair, and a moist feeling to skin, the content of an internal olefin sulfonate in which the sulfonate group is present at the C-2 position in the component (A) is preferably 25% by mass or less, more preferably 24% by mass or less, more preferably 23% by mass or less, more preferably 22% by mass or less, more preferably 20% by mass or less, more preferably less than 20% by mass, more preferably 19% by mass or less, and even more preferably 18% by mass or less. Also, from the viewpoint of rinse feel, combability during rinsing hair, the content of an internal olefin sulfonate in which the sulfonate group is present at the C-2 position in the component (A) is preferably 17.5% by mass or less, more preferably 15% by mass or less, more preferably 12% by mass or less, and even more preferably 10% by mass or less. Also, from the viewpoint of reducing the production cost, improving productivity, and the viewpoint of durability of foam and manageability after drying hair, the lower limit of the content of an internal olefin sulfonate in which the sulfonate group is present at the C-2 position in the component (A) is preferably 5% by mass or more, more preferably 6% by mass or more. Also, from the viewpoint of durability of foam, and manageability after drying hair, the lower limit of the content of an internal olefin sulfonate in which the sulfonate group is present at the C-2 position in the component (A) is more preferably 7% by mass or more, more preferably 8% by mass or more, more preferably 9% by mass or more, more preferably 10% by mass or more, more preferably 12% by mass or more, more preferably 14% by mass or more, and even more preferably 16% by mass or more. Further, from the above points, the content of an internal olefin sulfonate in which the sulfonate group is present at the C-2 position in the component (A) is preferably 5% by mass or more and 25% by mass or less, more preferably 5% by mass or more and 24% by mass or less, more preferably 5% by mass or more and 23% by mass or less, more preferably 5% by mass or more and 22% by mass or less, more preferably 5% by mass or more and 20% by mass or less, more preferably 6% by mass or more and less than 20% by mass, more preferably 7% by mass or more and 19% by mass or less, and even more preferably 8% by mass or more and 18% by mass or less.

Also, from the viewpoint of rinse feel, combability during rinsing hair, the content of an internal olefin sulfonate in which the sulfonate group is present at the C-2 position in the component (A) is preferably 9% by mass or more and 17.5% by mass or less, more preferably 9% by mass or more and 15% by mass or less, more preferably 9% by mass or more and 12% by mass or less, and even more preferably 9% by mass or more and 10% by mass or less. Also, from the viewpoint of durability of foam and manageability after drying hair, the content of an internal olefin sulfonate in which the sulfonate group is present at the C-2 position in the component (A) is preferably 9% by mass or more and 18% by mass or less, more preferably 10% by mass or more and 18% by mass or less, more preferably 12% by mass or more and 18% by mass or less, more preferably 14% by mass or more and 18% by mass or less, and even more preferably 16% by mass or more and 18% by mass or less.

It should note that the content of an internal olefin sulfonate in which the sulfonate group is present at the C-2 position in the component (A) may be measured by a method such as nuclear magnetic resonance spectroscopy. More specifically, it may be measured by a method using gas chromatography described later in Example.

Also, from the viewpoint of improving lathering property, foam quality, durability of foam and a rinse feel as well as imparting to hair combability and softness from during rinsing to after drying and manageability after drying, and imparting a moist feeling to skin, the content of an internal olefin sulfonate in which the sulfonate group is present at the C-1 position of the olefin chain or alkane chain in the component (A) is preferably 3.0% by mass or less, more preferably 2.5% by mass or less, more preferably 2.0% by mass or less, more preferably 1.5% by mass or less, and even more preferably 1.0% by mass or less. From the viewpoint of reducing the production cost and improving productivity, the lower limit of the aforementioned content is preferably 0.01% by mass or more.

Further, from the viewpoint of improving lathering property, foam quality, durability of foam and a rinse feel as well as imparting good combability after rinsing and manageability after drying to hair, and a moist feeling to skin, the content of an internal olefin sulfonate in which the sulfonate group is present further inside than the C-3 position of the olefin chain or alkane chain in the component (A) is preferably 70% by mass or more, more preferably 75% by mass or more, and even more preferably 80% by mass or more.

The internal olefin sulfonate is preferably a mixture of the hydroxy form and the olefin form. From the viewpoint of improving productivity and reducing impurities, the mass content ratio (hydroxy form/olefin form) of the hydroxy form of an internal olefin sulfonate to the olefin form of an internal olefin sulfonate in the component (A) or the cleansing composition is preferably from 50/50 to 100/0, more preferably from 60/40 to 100/0, more preferably from 70/30 to 100/0, more preferably from 75/25 to 100/0, and even more preferably from 75/25 to 95/5.

The mass content ratio of the hydroxy form of an internal olefin sulfonate to the olefin form of an internal olefin sulfonate in the component (A) or the cleansing composition may be obtained by separating the hydroxy form and the olefin form from the component (A) or the produced cleansing composition by HPLC and then measuring the separated substances by the method described in Examples.

From the viewpoint of environmental stability, low irritation, and the like, and also from the viewpoint of improving a durability of foam and rinse feel as well as imparting to hair combability and softness from during rinsing to after drying and manageability after drying, and imparting a moist feeling to skin, the content of the aforementioned component (A) in the cleansing composition of the present invention is preferably 0.1% by mass or more, more preferably 1% by mass or more, more preferably 2% by mass or more, and even more preferably 5% by mass or more, and from the viewpoint of improving a durability of foam and rinse feel as well as imparting to hair combability and softness from during rinsing to after drying and manageability after drying, and imparting a moist feeling to skin, the content of the aforementioned component (A) in the cleansing composition of the present invention is preferably 80% by mass or less, more preferably 50% by mass or less, more preferably 30% by mass or less, and even more preferably 20% by mass or less. Also, from the viewpoint of above points, the content of the aforementioned component (A) in the cleansing composition of the present invention is preferably 0.1% by mass or more and 80% by mass or less, more preferably 1% by mass or more and 50% by mass or less, more preferably 2% by mass or more and 30% by mass or less, and even more preferably 5% by mass or more and 20% by mass or less.

The internal olefin sulfonate (A) is obtainable by sulfonating a raw material internal olefin having 12 to 24 carbon atoms, followed by neutralization and hydrolysis. No particular limitation is imposed on the conditions of sulfonation, neutralization, and hydrolysis, and for example, the conditions described in U.S. Pat. Nos. 1,633,184 and 2,625,150, and Tenside Surf. Det. 31 (5) 299 (1994) may be referred to.

As mentioned above, in the present invention, a raw material internal olefin refers to an olefin substantially having a double bond inside the olefin chain. From the viewpoint of the lathering property, durability of foam and rinse feel of the cleansing composition, and imparting to hair combability and softness from during rinsing to after drying and manageability after drying, and imparting a moist feeling to skin, the number of carbon atoms in the raw material internal olefin is preferably from 12 to 24, more preferably from 12 to 20, more preferably from 12 to 18, more preferably from 14 to 18, and even more preferably from 16 to 18. An internal olefin to be used as the raw material may be used singly, or a combination of two or more thereof may be used.

From the viewpoint of acquiring lathering property and a creamy foam quality for easy washing, improving a durability of foam and rinse feel, and imparting to hair combability and softness from during rinsing to after drying and manageability after drying, and imparting a moist feeling to skin, the content of an internal olefin in which the double bond is present at the C-2 position in the raw material internal olefin is preferably 40% by mass or less, more preferably 35% by mass or less, more preferably 32% by mass or less, more preferably 30% by mass or less, even more preferably 27% by mass or less, and also, from the viewpoint of rinse feel, combability during rinsing hair, it is preferably 25% by mass or less, more preferably 20% by mass or less, more preferably less than 20% by mass, more preferably 19% by mass or less, and even more preferably 18% by mass or less. Also, from the viewpoint of reducing the production cost and improving productivity, and from the viewpoint of durability of foam and manageability after drying hair, the lower limit of the aforementioned content is preferably 5% by mass or more, more preferably 6% by mass or more, more preferably 7% by mass or more, more preferably 8% by mass or more, more preferably 9% by mass or more, more preferably 12% by mass or more and even more preferably 15% by mass or more, and further, from the viewpoint of durability of foam and manageability after drying hair, it is preferably 20% by mass or more, more preferably 22% by mass or more, and even more preferably 24% by mass or more. Also, from the above points, the content of an internal olefin in which the double bond is present at the C-2 position in the raw material internal olefin is preferably 5% by mass or more and 40% by mass or less, more preferably 5% by mass or more and 35% by mass or less, more preferably 5% by mass or more and 32% by mass or less, more preferably 5% by mass or more and 30% by mass or less, more preferably 6% by mass or more and 30% by mass or less, more preferably 7% by mass or more and 30% by mass or less, more preferably 8% by mass or more and 30% by mass or less, more preferably 9% by mass or more and 30% by mass or less, more preferably 12% by mass or more and 30% by mass or less, and even more preferably 15% by mass or more and 27% by mass or less.

From the viewpoint of rinse feel and combability during rinsing hair, the content of an internal olefin in which the double bond is present at the C-2 position in the raw material internal olefin is preferably 15% by mass or more and 25% by mass or less, more preferably 15% by mass or more and 20% by mass or less, more preferably 15% by mass or more and less than 20% by mass, more preferably 15% by mass or more and 19% by mass or less, and even more preferably 15% by mass or more and 18% by mass or less. Also, from the viewpoint of durability of foam, manageability after drying hair, the content of an internal olefin in which the double bond is present at the C-2 position in the raw material internal olefin is preferably 20% by mass or more and 27% by mass or less, more preferably 22% by mass or more and 27% by mass or less, and even more preferably 24% by mass or more and 27% by mass or less.

Also, from the viewpoint of improving lathering property, foam quality, durability of foam and a rinse feel as well as imparting to hair combability and softness from during rinsing to after drying and manageability after drying, and imparting a moist feeling to skin, the content of an olefin in which the double bond is present at the C-1 position, namely α-olefin, in the raw material internal olefin is preferably 3.0% by mass or less, more preferably 2.5% by mass or less, more preferably 2.0% by mass or less, more preferably 1.5% by mass or less, and even more preferably 1.0% by mass or less. From the viewpoint of reducing the production cost and improving productivity, the lower limit of the aforementioned content is preferably 0.01% by mass or more.

Further, from the viewpoint of improving lathering property, foam quality, durability of foam and a rinse feel as well as imparting to hair combability and softness from during rinsing to after drying and manageability after drying, and imparting a moist feeling to skin, the total content of a raw material internal olefin in which the double bond is present further inside than the C-3 position in the raw material internal olefin is preferably 65% by mass or more, more preferably 70% by mass or more, more preferably 75% by mass or more, and even more preferably 80% by mass or more.

The distribution of the double bond in the raw material internal olefin may be measured by a method described in Examples using a gas chromatograph mass spectrometer (hereinbelow, abbreviated as GC-MS). Specifically, components each having different carbon chain lengths and double bond positions are accurately separated by a gas chromatograph analyzer (hereinbelow, abbreviated as GC), and each component is then analyzed by a mass spectrometer (hereinbelow, abbreviated as MS) to identify the position of double bond, and from the resulting GC peak area, the fraction of each component may be found out.

The aforementioned sulfonation reaction may be carried out by reacting a sulfur trioxide gas with an internal olefin at a ratio of from 1.0 to 1.2 moles of sulfur trioxide per mole of the raw material internal olefin. The reactions are preferably carried out at a reaction temperature of 20 to 40° C.

Neutralization is carried out by reacting from 1.0 to 1.5 times the molar amount of an alkali agent such as sodium hydroxide, ammonia, or 2-aminoethanol with the theoretical value of sulfonate group.

The hydrolysis reaction may be carried out at from 90 to 200° C. for from 30 minutes to three hours in the presence of water. These reactions may be successively carried out. Also, upon completion of the reactions, the products may be purified by extraction, washing, and the like.

Also, in the production of the internal olefin sulfonate (A), the raw material internal olefin in which the number of carbon atoms is distributed in from 12 to 24 may be subjected to sulfonation, neutralization, and hydrolysis, or the raw material internal olefin having a uniform number of carbon atoms may be subjected to sulfonation, neutralization, and hydrolysis. Also, a plurality of internal olefin sulfonates each having different numbers of carbon atoms may be produced in advance and then mixed, as needed.

As the internal olefin sulfonate composition (A) of the present invention is obtained by sulfonating an internal olefin, followed by neutralization and hydrolysis as described above, an unreacted raw material internal olefin and inorganic compounds may remain in the composition (A). It is preferred that the contents of these components are much smaller.

The content of the raw material internal olefin in the component (A) of the present invention is preferably less than 5.0% by mass, more preferably less than 3.0% by mass, more preferably less than 1.5% by mass, and even more preferably less than 1.0% by mass in the component (A), from the viewpoint of improving durability of foam and rinse feel, and imparting to hair good combability and softness during rinsing and imparting moist feeling to skin.

The content of the unreacted internal olefin may be measured by a method described later in Examples.

The content of the inorganic compounds in the component (A) of the present invention is preferably less than 7.5% by mass, more preferably less than 5.0% by mass, more preferably less than 3.0% by mass, more preferably less than 2.0% by mass, and even more preferably less than 1.6% by mass in the component (A), from the viewpoint of improving durability of foam and rinse feel, and imparting to hair good combability and softness during rinsing and imparting moist feeling to skin.

In this context, the inorganic compounds include sulfates and alkali agents. The content of these inorganic compounds may be measured by a potentiometric titration. Specifically, the content may be measured by a method described later in Examples.

The cleansing composition of the present invention may contain a surfactant (hereinbelow, may also be referred to as a component (B)) other than the aforementioned component (A), so long as the effects of the present invention are not impaired.

As the surfactant other than the aforementioned component (A), any surfactant which is normally used in pharmaceutical products, quasi-drugs, cosmetics, toiletries, general merchandise, and the like may be used, and specific examples thereof include an anionic surfactant, a nonionic surfactant, an amphoteric surfactant, and a cationic surfactant other than the aforementioned component (A). From the viewpoint of improving the cleansing property, foamability, and foam quality, the surfactant other than the aforementioned component (A) is preferably a nonionic surfactant or an amphoteric surfactant other than the aforementioned (A).

From the viewpoint of improving the lathering property and cleansing property, the anionic surfactant other than the aforementioned component (A) is preferably a sulfuric acid ester salt, a sulfonic acid salt, a carboxylic acid salt, a phosphoric acid ester salt, and an amino acid salt. Specific examples thereof include a sulfuric acid ester salt such as alkyl sulfate, alkenyl sulfate, polyoxyalkylene alkyl ether sulfate, polyoxyalkylene alkenyl ether sulfate, and polyoxyalkylene alkyl phenyl ether sulfate; a sulfonic acid salt such as sulfosuccinic acid alkyl ester salt, polyoxyalkylene sulfosuccinic acid alkyl ester salt, alkane sulfonate, acyl isethionate and acyl methyl taurate; a higher fatty acid salt having from 8 to 16 carbon atoms; a phosphoric acid ester salt such as alkyl phosphate and polyoxyalkylene alkyl ether phosphate; and an amino acid salt such as acyl glutamate, an alanine derivative, a glycine derivative, and an arginine derivative.

Also, from the viewpoint of cleansing property, foamability, and foam quality, and from the viewpoint of imparting to hair combability and softness from during rinsing to after drying and manageability after drying, and imparting a moist feeling to skin, the aforementioned anionic surfactant preferably has an alkyl group or alkenyl group having from 8 to 20 carbon atoms, and more preferably has an alkyl group or alkenyl group having from 10 to 16 carbon atoms.

Among such anionic surfactants, alkyl sulfate such as sodium lauryl sulfate, polyoxyethylene alkyl ether sulfate such as sodium polyoxyethylene lauryl ether sulfate, a higher fatty acid salt such as potassium laurate, a sulfosuccinic acid alkyl ester salt such as sodium polyoxyethylene lauryl ether sulfosuccinnate, acyl glutamate such as sodium N-acyl-L glutamate, an acyl sarcosinine salt, acyl glycine salt, acyl isethionate, acyl methyl taurate, or alkyl phosphate is preferable, and sodium lauryl sulfate, ammonium polyoxyethylene (1) lauryl ether sulfate (ammonium laureth-1 sulfate), sodium polyoxyethylene (2) lauryl ether sulfate (sodium laureth-2 sulfate), potassium laurate, sodium polyoxyethylene lauryl ether (2) sulfosuccinate (sodium laureth-2 sulfosuccinate), or sodium cocoyl glutamate is more preferable.

From the viewpoint of improving cleansing property and the stability of the cleansing composition, examples of the aforementioned nonionic surfactant include a polyethylene glycol type nonionic surfactant such as polyoxyethylene sorbitan fatty acid ester, polyoxyethylene sorbitol fatty acid ester, polyoxyethylene glycerin fatty acid ester, polyoxyethylene fatty acid ester, polyoxyethylene alkyl ether, polyoxyethylene alkyl phenyl ether, or polyoxyalkylene (hydrogenated) castor oil, a polyhydric alcohol type nonionic surfactant such as sucrose fatty acid ester, polyglycerol alkyl ether, polyglycerol fatty acid ester, or alkyl glycoside, and fatty acid alkanolamide.

The nonionic surfactant preferably has an alkyl group or alkenyl group having from 8 to 20 carbon atoms as the hydrophobic moiety from the viewpoint of cleansing property of the cleansing composition according to the present invention and the volume and quality of foam during cleansing, and from the viewpoint of imparting to hair combability and softness from during rinsing to after drying and manageability after drying, and imparting a moist feeling to skin.

Among such nonionic surfactants, alkyl glycoside having from 8 to 18 carbon atoms, preferably from 8 to 12 carbon atoms such as decyl glucoside, polyoxyalkylene alkyl ether such as polyoxyethylene lauryl ether, and fatty acid monoalkanolamide such as coconut oil fatty acid monoethanolamide are preferable, and decyl glucoside, polyoxyethylene (3) lauryl ether (laureth-3), polyoxyethylene (16) myristyl ether (ceteareth-16), polyoxypropylene (5) polyoxyethylene (20) cetyl ether, polyoxyethylene (9) lauryl ether, polyoxyethylene (7), alkyl ether having from 11 to 15 carbon atoms, coconut oil fatty acid monoethanolamide, or coconut oil fatty acid N-methyl monoethanolamide is more preferable.

From the viewpoint of improving stability of foam and feel during rinsing, examples of the aforementioned amphoteric surfactant include a betaine surfactant such as imidazoline betaine, alkyldimethylaminoacetate betaine, fatty acid amidopropyl betaine, or sulfobetaine, and an amine oxide surfactant such as alkyl dimethyl amine oxide.

Among such amphoteric surfactants, from the viewpoint of cleansing property of the cleansing composition according to the present invention and the volume and quality of foam during cleansing, and from the viewpoint of imparting to hair combability and softness from during rinsing to after drying and manageability after drying, and imparting a moist feeling to skin, imidazoline betaine, sulfobetaine, fatty acid amidopropyl betaine, and the like are preferable, and specifically, coconut oil fatty acid amidopropyl betaine, lauryl carbomethoxy methyl hydroxy imidazolium betaine, or lauryl hydroxy sulfobetaine is more preferable.

From the viewpoint of improving foam quality, softness of hair, and moist feeling of skin, examples of the aforementioned cationic surfactant include a mineral acid or organic acid salt of the tertiary amine represented by the following general formula (1) and a quaternary ammonium salt-type surfactant represented by the following general formula (2).

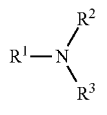

(1)

(wherein $R^1$ represents a linear or branched alkyl group or alkenyl group having from 6 to 28 carbon atoms which may be interrupted by an amide group, an ester group, or an ether group, and $R^2$ represents a linear or branched alkyl group, alkenyl group, or alkanol group having from 1 to 28 carbon atoms which may be interrupted by an amide group, an ester group, or an ether group, and $R^3$ represents a linear or branched alkyl group or alkanol group having from 1 to 3 carbon atoms.)

In the general formula (1), from the viewpoint of imparting to hair combability and softness from during rinsing to after drying and manageability after drying, and imparting a moist feeling to skin, the number of carbon atoms in $R^1$ is preferably from 12 to 28, more preferably from 14 to 25, and even more preferably from 16 to 25. From a similar viewpoint, the number of carbon atoms in $R^2$ is preferably from 12 to 28, more preferably from 14 to 25, and even more preferably from 16 to 25, or $R^2$ is preferably a methyl group, an ethyl group, or a hydroxyethyl group. From a similar viewpoint, $R^3$ is preferably a methyl group, an ethyl group, or a hydroxyethyl group.

No particular limitation is imposed on the mineral acid or organic acid which forms a salt with the tertiary amine represented by the general formula (1); from the viewpoint of dispersion stability of a surfactant, hydrogen halide, sulfuric acid, acetic acid, citric acid, lactic acid, glutamic acid, and alkyl sulfate having from 1 to 3 carbon atoms are preferable, and from the viewpoint of chemical stability, hydrogen halide is preferably hydrogen chloride.

(2)

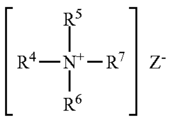

(wherein $R^4$ represents a linear or branched alkyl group or alkenyl group having from 6 to 28 carbon atoms which may be interrupted by an amide group, an ester group, or an ether group, $R^5$ represents a linear or branched alkyl group, alkenyl group, or alkanol group having from 1 to 28 carbon atoms which may be interrupted by an amide group, an ester group, or an ether group, $R^6$ and $R^7$ each represent a linear or branched alkyl group having from 1 to 3 carbon atoms, and $Z^-$ represents an anionic group, which is the counter ion of an ammonium salt.)

In the general formula (2), from the viewpoint of imparting to hair combability and softness from during rinsing to after drying and manageability after drying, and imparting a moist feeling to skin, a preferred embodiment of $R^4$ is the same as a preferred embodiment of $R^1$ in the general formula (1). From a similar viewpoint, a preferred embodiment of $R^5$ is the same as a preferred embodiment of $R^2$ in the general formula (1). Also, from a similar viewpoint, $R^6$ and $R^7$ are each preferably a methyl group or an ethyl group.

No particular limitation is imposed on $Z^-$ as long as it is an anionic group. Specific examples thereof include an alkyl sulfate ion, a sulfate ion, a phosphate ion, alkyl carboxylate ion, and a halide ion. Among them, from the viewpoint of easiness of production and availability, a halide ion is preferable. Examples of the halide ion include a fluoride ion, a chloride ion, a bromide ion, and an iodide ion, and from the viewpoint of chemical stability, a chloride ion or a bromide ion is preferable, of which a chloride ion is more preferable.

Examples of the mineral acid or organic acid salt of the tertiary amine represented by the general formula (1) and the quaternary ammonium salt-type surfactant represented by the general formula (2) include mono long-chain alkyl trimethyl ammonium chloride, di long-chain alkyl dimethyl ammonium chloride, and a long-chain tertiary amine salt. Specific examples include mono long-chain alkyl trimethyl ammonium chloride such as stearyl trimethyl ammonium chloride, behenyl trimethyl ammonium chloride, cetyl trimethyl ammonium chloride, and stearoxy propyl trimethyl ammonium chloride; di long-chain alkyl dimethyl ammonium chloride such as distearyl dimethyl ammonium chloride and diisostearyl dimethyl ammonium chloride; mono long-chain dimethylamine such as stearyl dimethylamine, behenyl dimethylamine, octadecyloxypropyl dimethylamine, stearamidoethyl diethylamine, stearamidopropyl dimethylamine, and behenamidopropyl dimethylamine, a glutamic acid salt, a hydrochloric acid salt, a citric acid salt, or a lactic acid salt and the like of mono long-chain diethylamine, and also, from the viewpoint of imparting to hair combability and softness from during rinsing to after drying and manageability after drying, and imparting a moist feeling to skin, behenyl trimethyl ammonium chloride, cetyl trimethyl ammonium chloride, stearoxy propyl trimethyl ammonium chloride, stearyl dimethylamine, stearamidopropyl dimethylamine, and behenamidopropyl dimethylamine are preferable.

From the viewpoint of improving durability of foam and rinse feel, imparting to hair combability and softness from during rinsing to after drying and manageability after drying, and imparting a moist feeling to skin, the content of the aforementioned component (B) in the cleansing composition of the present invention is preferably 50% by mass or less, more preferably 30% by mass or less, more preferably 20% by mass or less, more preferably 15% by mass or less, and even more preferably 10% by mass or less, and preferably 0.1% by mass or more, more preferably 0.5% by mass or more, and even more preferably 1.0% by mass or more.

The mass content ratio of the component (A) to the component (B) [component (A)/component (B)] is preferably from 1000 to 0.01, more preferably from 100 to 0.1, more preferably to 0.5, and even more preferably from 5 to 1 from the viewpoint of improving the durability of foam and rinse feel in treatment with the cleansing composition, imparting to hair combability and softness from during rinsing to after drying and manageability after drying, and imparting a moist feeling to skin.

Preferably, the cleansing composition according to the present invention further contains a moisturizing agent (hereinafter, also referred to as a component (C)) from the viewpoint of improving the durability of foam and rinse feel in treatment with the cleansing composition, imparting to hair combability and softness from during rinsing to after drying and manageability after drying, and imparting a moist feeling to skin.

Examples of preferable moisturizing agents as the component (C) include one or more selected from ceramides, plant extracts, sodium hyaluronate, propylene glycol, 1,3-butylene glycol, glycerol and derivatives thereof, sorbitol and derivatives thereof, sodium lactate, sodium pyrrolidonecarboxylate, carbitol, diethylene glycol monomethyl ether, sugar alcohols (such as maltitol, xylitol, sorbitol, erythritol, and lactitol), medium-chain fatty acid triglycerides, and urea, or include other moisturizing agent. Ceramides, plant extracts, sodium hyaluronate, glycerol and derivatives thereof are preferable. Examples of the derivatives of glycerol include polyoxyethylene (26) glyceryl ether.

The ceramides include natural ceramides, synthetic ceramides, and analogs thereof obtained by synthesis and the like (pseudo-ceramides). Examples of such ceramides include Ceramide H03 (Sederma), Ceramide II (Sederma), Questamide H (Quest), Ceramide TIC-001 (TAKASAGO INTERNATIONAL CORPORATION), and SOFCARE Ceramide SL-E (Kao Corporation) and the like. Particularly preferable examples of the ceramide analogs obtained by synthesis include amide derivatives including the SOF-CARE Ceramide SL-E, which are represented by the general formula (3) below:

(3)

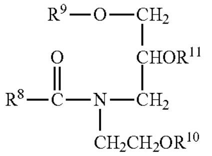

[wherein $R^8$ and $R^9$ may be the same or different, and represent a linear or branched saturated or unsaturated hydrocarbon group having 7 to 39 carbon atoms and optionally substituted one or more hydroxy groups; $R^{10}$ and $R^{11}$ may be the same or different, represent a hydrogen atom, phosphoric acid salt residue, sulfuric acid salt residue, or sugar residue. It should be noted that it has one or more hydroxy groups in one molecule.]

In the general formula (3), the hydrocarbon group in $R^8$ is preferably a linear or branched saturated or unsaturated hydrocarbon group having from 9 to 25 carbon atoms. The hydrocarbon group in $R^9$ is preferably a linear or branched saturated or unsaturated hydrocarbon group having from 10 to 26 carbon atoms. $R^{10}$ and $R^{11}$ are preferably a hydrogen atom.

The method for producing the amide derivative (3) is described in JP-A-62-228048, JP-A-63-216852, and the like in detail.

The ceramides may be used alone or in combination of two or more kinds. From the viewpoint of blend stability and moisturizing effect, the content of the ceramides to be blended in the cleansing composition according to the present invention is preferably from 0.001 to 30% by mass, more preferably from 0.01 to 5% by mass, and even more preferably from 0.1 to 3% by mass. Additionally, the ceramides may be any form of soluble ceramides, emulsified ceramides, liquid crystallized ceramides, and a dispersion liquid. In the case of the dispersion liquid, the ceramides are preferably those which are solid at room temperature (25° C.). From the viewpoint of blend stability when the cleansing composition is produced, the ceramides are preferably those which have a melting point of 30° C. or more, and more preferably a melting point of 40° C. or more. In the case of the dispersion liquid, the ceramides have an average particle size of preferably from 0.5 to 150 μm, more preferably from 1 to 150 μm, and even more preferably from 1 to 80 μm. The average particle size used therein is an arithmetic average value of values obtained as follows: a photograph is taken under transmitted light using an optical microscope; and 30 particles on the photograph are arbitrarily selected; in each of the particles, the longest portion as a linear dimension is measured.

Examples of the plant extracts include plant extracts available from ICHIMARU PHARCOS Co., Ltd. such as aloe, aloe vera, ginkgo (*Ginkgo biloba*), fennel (*Foeniculum vulgare*), seaweed, puerariae radix (*Pueraria lobata*), chamomile, kiwifruit (*Actinidia deliciosa*), cucumber, loofah (luffa), cape jasmine (*Gardenia jasminoides*), rice bran, peach, yuzu (Citrus junos), and hatomugi (*Coix lacryma-jobi* var. ma-yuen). Preferably, the content of the plant extracts to be contained in the cleansing composition according to the present invention is preferably from 0.001 to 10% by mass, more preferably from 0.005 to 5% by mass, and even more preferably from 0.01 to 3% by mass from the viewpoint of blend stability and moisturizing effect. If the cleansing composition contains the plant extracts, not only the moisturizing effect but also an anti-inflammatory effect and the like unique to the extract are given. Preferably, the content of sodium hyaluronate as the moisturizing agent to be contained in the composition according to the present invention is from 0.001 to 10% by mass, more preferably from 0.01 to 5% by mass, and even more preferably from 0.05 to 1% by mass from the viewpoint of blend stability and the moisturizing effect.

The mass content ratio of the component (A) to the component (C) [component (A)/component (C)] is preferably from 500 to 0.01, more preferably from 200 to 0.1, and even more preferably from 50 to 5 from the viewpoint of improving durability of foam and rinse feel, imparting to hair combability and softness from during rinsing to after drying and manageability after drying, and imparting a moist feeling to skin. The content of the component (C) is preferably from 0.001 to 30% by mass, and more preferably from 0.01 to 5% by mass in the cleansing composition according to the present invention from the viewpoint of blend stability and the moisturizing effect. The moisturizing agents as the component (C) may be used alone or in combination of two or more kinds.

Preferably, the cleansing composition according to the present invention further contains an antibacterial agent or an anti-dandruff agent (hereinafter, also referred to as a component (D)) from the viewpoint of improving the durability of foam and rinse feel in treatment with the cleansing composition, imparting to hair combability and softness from during rinsing to after drying and manageability after drying, imparting a moist feeling to skin, improving a deodorant effect, and reducing itching after cleansing.

Examples of the antibacterial agent as the component (D) include triclosan, triclocarban, piroctone olamine, zinc pyrithione, selenium disulfide, 3-methyl-4-(1-methylethyl)phenol and the like, and antibacterial agents described in Koushouhin Iyakuhin Bofusakkinzainadono Kagaku (edited by John J. Cabala, Fragrance Journal Ltd.). Among these, triclosan, triclocarban, piroctone olamine, and zinc pyrithione are more preferable. In the case where the cleansing composition according to the present invention is applied to a cleansing composition for hair which is used without washing off the cleansing composition, use of triclosan, triclocarban, or piroctone olamine is preferable from the viewpoint that the feel of hair is not impaired.

Among these components (D), examples of cationic antibacterial agents include quaternary ammonium salts represented by the general formula (4):

(4)

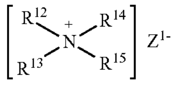

($R^{12}$ and $R^{13}$ represent a long-chain alkyl group, long-chain alkenyl group, or long-chain hydroxyalkyl group each having from 6 to 14 carbon atoms and from 16 to 26 carbon atoms in total, and may be the same or different from each other; $R^{14}$ and $R^{15}$ represent an alkyl group or hydroxyalkyl group having from 1 to 3 carbon atoms, or a polyoxyethylene group having the average number of moles added of 10 or less, and may be the same or different from each other; $Z^1$ represents a halogen atom, amino acid, fatty acid, an anionic residue of phosphoric acid ester, phosphonic acid ester, sulfonic acid ester, or sulfuric acid ester having a linear or branched alkyl group or alkenyl group having from 1 to 30 carbon atoms, or an anionic oligomer or polymer containing a formalin condensate of a sulfonated polycyclic aromatic compound optionally having styrene sulfonic acid having a polymerization degree of 3 or more or a hydrocarbon group as a substituent);

benzalkonium salts and benzethonium salts represented by the general formula (5):

(5)

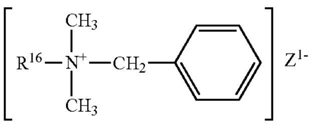

(wherein $R^{16}$ represents a hydrocarbon group having from 8 to 14 carbon atoms or a group represented by:

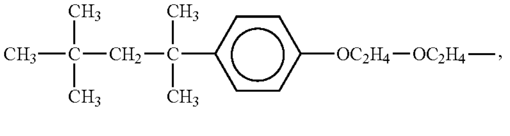

and $Z^1$ represents the same as above);

chlorhexidine salts represented by the general formula (6):

(6)

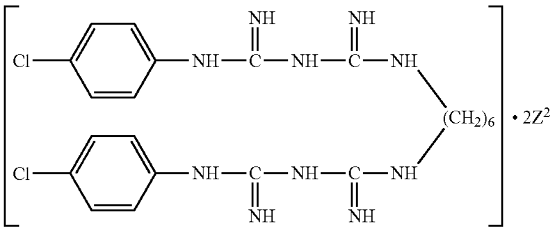

(wherein $Z^2$ represents gluconic acid, acetic acid, or hydrochloric acid);

and pyridinium salts represented by the general formula (7):

(7)

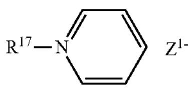

(wherein $R^{17}$ represents a linear or branched alkyl group having from 6 to 18 carbon atoms, and $Z^1$ represents the same as above), and the like.

As $Z^1$ in the general formulas (4), (5), and (7) above, a halogen atom is more preferable.

Suitable specific examples of a cationic antibacterial agent include benzalkonium chloride, benzethonium chloride, cetylpyridinium chloride, chlorhexidine gluconate, chlorhexidine acetate, and chlorhexidine hydrochloride and the like. Further, those represented by the general formula (5) such as benzalkonium chloride and benzethonium chloride are preferable.

The antibacterial agents and cationic antibacterial agents as the component (D) may be used alone or in combination. Use of a combination of the antibacterial agent with the cationic antibacterial agent can provide a higher effect. From the viewpoint of improving durability of foam and rinse feel, imparting to hair combability and softness from during rinsing to after drying and manageability after drying, imparting a moist feeling to skin, improving a deodorant effect, and reducing itching, the content of the component (D) to be blended with the cleansing composition according to the present invention is preferably from 0.005 to 5% by mass, more preferably from 0.01 to 3% by mass, and even more preferably from 0.05 to 2% by mass. The mass content ratio of the component (A) to the component (D) is preferably from 200 to 0.1, more preferably from 100 to 1, and even more preferably from 50 to 5.

From the viewpoint of improving the appearance, preferably, the cleansing composition according to the present invention further contains a pearling agent (hereinafter, also referred to as a component (E)).

The pearling agent as the component (E) is a component that can give pearl-like gloss to the appearance of the cleansing composition. In the present invention, emulsifying agents such as esters (such as monoester and diester) of glycol and fatty acid and long-chain dialkyl ethers, water-insoluble inorganic salts, or compounds known as the pearling agent may be used. Specifically, examples of the pealing agents include organic compounds such as ethylene glycol distearate, ethylene glycol monostearate, diethylene glycol distearate, ethylene glycol dipalmitate, and distearyl ether. From the viewpoint of cost and availability, esters of glycol and fatty acid are suitable. Among these, ethylene glycol monostearate, ethylene glycol distearate are preferable, and ethylene glycol distearate is more preferable. Examples of the water-insoluble inorganic salts include titanium oxide, tin oxide, and mica and the like.

From the viewpoint of economy, cleansing property, and the appearance, the content of the component (E) is preferably not less than 0.3% by mass and not more than 10% by mass, more preferably not less than 0.5% by mass and not more than 5.0% by mass, and even more preferably from not less than 1.0% by mass and not more than 2.0% by mass in the cleansing composition according to the present invention.

In the present invention, the pearling agent as the component (E) may be directly added to the cleansing composition for skin or hair. Alternatively, a pearl component may be crystallize in advance to prepare a premix (pearling agent mixture), and then the premix may be added to the cleansing composition.

The component (A) as a pearl crystal precipitating aid may be used for the pearling agent mixture used as the component (E). From the viewpoint of crystal stability of the pearling agent mixture and improvement in dispersibility when the pearling mixture is added to the cleansing composition, the mass content ratio of the component (A) to the component (E) in the pearling agent mixture as the component (E) [component (A)/component (E)] is preferably from 20 to 0.1, more preferably from 10 to 1, and even more preferably from 7 to 3.

From the viewpoint of improving the durability of foam and rinse feel in treatment with the cleansing composition, imparting to hair combability and softness from during rinsing to after drying and manageability after drying, imparting a moist feeling to skin, and improving a long-lasting effect of the feel, preferably, the cleansing composition according to the present invention further contains a fragrance (hereinafter, also referred to as a component (F)).

Examples of the fragrance used as the component (F) include one or two or more selected from the group consisting of citrus fragrances (F1), floral fragrances (F2), woody fragrances (F3), fruity fragrances (F4), spicy fragrances (F5), musk fragrances (F6), green fragrances (F7), and others (F8). From the viewpoint of the long-lasting effect of the fragrance after use, among these, preferable fragrances as the component (F) are: (F1) limonene, (F2) linalool, linalyl acetate, citronellol, phenylethyl alcohol, methyl dihydrojasmonate, lyral, γ-methyl ionone, and β-ionone, (F3) ambroxan and p-t-butylcyclohexyl acetate, (F4) o-t-butylcyclohexyl acetate, damascone, and γ-undecalactone, (F5) eugenol, (F6) PEARLIDE and tentarome, and (F7) helional, tripural, menthol, and camphor. The proportion of the fragrance is preferably from 0.05 to 3.0% by mass, and more preferably from 0.1 to 1.0% by mass. The mass content ratio of the component (A) to the component (F) [component (A)/component (F)] is preferably from 150 to 0.5, more preferably from 40 to 5, and even more preferably from 10 to 1 from the viewpoint of improving durability of foam and rinse feel, imparting to hair combability and softness from during rinsing to after drying and manageability after drying, imparting a moist feeling to skin, and the long-lasting effect of the fragrance.

From the viewpoint of improving stability of the appearance, viscosity, smell, and the like, preferably, the cleansing composition according to the present invention further contains an organic solvent (hereinafter, also referred to as a component (G)). Examples of the organic solvent used include aromatic alcohols, carbonates, or a hydroxy compound represented by the general formula (8) below:

$$HO\text{-}(AO)_r\text{-}R^{18} \qquad (8)$$

(wherein $R^{18}$ represents a hydrogen atom or an linear or branched alkyl group or alkenyl group having from 1 to 4 carbon atoms; A represents an alkylene group having from 2 to 4 carbon atoms; the average number r of moles added represents the number of from 1 to 3000, the r number of A may be the same or different, and A has any disposition).

Examples of the aromatic alcohol include benzyl alcohol, benzyloxyethanol, and phenoxyethanol. Examples of carbonates include alkylene carbonates such as ethylene carbonate and propylene carbonate.

A preferable hydroxy compound represented by the general formula (8) above is those in which A is an linear or branched alkylene group having 2 or 3 carbon atoms, and more preferably a linear or branched alkylene group having 3 carbon atoms; $R^{18}$ is hydrogen, a linear alkyl group or alkenyl group having from 2 to 4 carbon atoms, and more preferably hydrogen or a linear alkyl group having 2 or 3 carbon atoms; r is from 1 to 1000 (the average number of moles added), and more preferably from 1 to 100 (the average number of moles added).

Specific examples of the hydroxy compound represented by the general formula (8) include ethylene glycol, diethylene glycol, polyethylene glycol, propylene glycol, dipropylene glycol, polypropylene glycol, diethylene glycol monomethyl ether, diethylene glycol monoethyl ether, diethylene glycol monopropyl ether, and diethylene glycol monobutyl ether and the like.

An organic solvent as the component (G) is preferably benzyl alcohol, benzyloxyethanol, propylene carbonate, diethylene glycol monoethyl ether, diethylene glycol monobutyl ether, diethylene glycol, polyethylene glycol, dipropylene glycol, or polypropylene glycol, and more preferably, benzyl alcohol, diethylene glycol monoethyl ether, diethylene glycol monobutyl ether, polyethylene glycol, or polypropylene glycol from the viewpoint of improving the stability of the cleansing composition. In the case where the organic solvent as the component (G) is polyethylene glycol or polypropylene glycol, the weight average molecular weight (measurement method: GPC weight method) is preferably from 200 to 10000, more preferably from 200 to 4000, and even more preferably from 300 to 1500.

From the viewpoint of improvement in stability and cleansing property, the content of the component (G) is preferably from 0.1 to 30% by mass, more preferably from 0.2 to 10% by mass, and even more preferably from 0.3 to 2% by mass in the cleansing composition according to the present invention. From the viewpoint of improvement in stability and cleansing property, the mass content ratio of the component (A) to the component (G) [component (A)/component (G)] is preferably from 100 to 0.01, more preferably from 60 to 1, and even more preferably from 40 to 5.

From the viewpoint of imparting to hair combability and softness from during rinsing to after drying and manageability after drying, imparting a moist feeling to skin, and cares to damage, preferably, the cleansing composition according to the present invention further contains a vitamin agent (hereinafter, also referred to as a component (H)).

Examples of the vitamin agent include as the component (H) vitamins A such as retinol, retinol acetate, retinol palmitate, and β-carotene; vitamins B such as pyridoxine hydrochloride (vitamin B6), nicotinic acid derivatives (nicotinic acid amide, nicotinic acid benzyl ester), γ-oryzanol, riboflavin (vitamin B2), and vitamin B derivatives such as riboflavin acetic acid ester, pyridoxine dicaprylate, and pyridoxine dipalmitate; vitamins C such as ascorbic acid (vitamin C), monostearyl ascorbate, and ascorbic acid phosphoric acid ester; vitamins D such as ergocalciferol (vitamin D2); vitamins E such as dl-tocopherol (vitamin E), tocopherol acetate, and tocopherol nicotinate; pantothenic acids such as calcium pantothenate, pantothenic acid ethyl ether, and D-pantothenyl alcohol (D-panthenol); and vitamins H such as biotin.

From the viewpoint of cares of damaged hair and skin, the vitamin agent as the component (H) are preferably retinol, retinol palmitate, β-carotene, pyridoxine hydrochloride (vitamin B6), nicotinic acid amide, γ-oryzanol, riboflavin (vitamin B2), ascorbic acid (vitamin C), dl-tocopherol (vitamin E), tocopherol acetate, pantothenic acid ethyl ether, D-pantothenyl alcohol (D-panthenol), or biotin.

From the viewpoint of blend stability, cares of damaged hair and skin, imparting to hair combability and softness from during rinsing to after drying and manageability after drying, and imparting a moist feeling to skin, the content of the component (H) is preferably from 0.01 to 10% by mass, more preferably from 0.05 to 5% by mass, and even more preferably from 0.1 to 1% by mass in the cleansing composition according to the present invention.

From the viewpoint of imparting to hair combability and softness from during rinsing to after drying and manageability after drying, imparting a moist feeling to skin, and cares to damage, by the component (A) and the component (H), the mass content ratio of the component (A) to the component (H) [component (A)/component (H)] is preferably from 200 to 0.1, more preferably from 150 to 1, and even more preferably from 100 to 10.

From the viewpoint of improvement in stability and adjustment of viscosity, preferably, the cleansing composition according to the present invention further contains a thickener (hereinafter, also referred to as a component (I)).

Examples of the thickener as the component (I) include guar gum, locust bean gum, quince seed gum, carrageenan, galactan, gum arabic, tragacanth gum, pectin, mannan, starch, xanthan gum, dextran, succionoglucan, curdlan, hyaluronic acid, gelatin, casein, albumin, collagen, shellac, methyl cellulose, ethyl cellulose, hydroxyethyl cellulose, hydroxypropyl cellulose, carboxymethyl cellulose, methyl hydroxypropyl cellulose, soluble starch, carboxymethyl starch, methyl starch, hydroxypropyl starch, alginic acid propylene glycol ester, alginic acid salt, polyvinyl alcohol, polyvinylpyrrolidone, polyvinyl methyl ether, carboxyvinyl polymers, sodium polyacrylate, polyvinyl methacrylate, polyethylene oxide, ethylene oxide.propylene oxide block copolymers, polyglycol-polyamine condensates, polymethyl methacrylate fine particles, bentonite, laponite, fine powder of silicon oxide, colloidal alumina, or VEEGUM.

From the viewpoint of improvement in the stability of the cleansing composition and adjustment of viscosity, the content of the component (I) is preferably from 0.01 to 10% by mass, more preferably from 0.05 to 5% by mass, and even more preferably from 0.1 to 3% by mass in the cleansing composition according to the present invention. The mass content ratio of the component (A) to the component (I) [component (A)/component (I)] is preferably from 200 to 0.5, more preferably from 100 to 5, and even more preferably from 50 to 10.

From the viewpoint of improvement in the feel and viscosity stability, preferably, the cleansing composition according to the present invention further contains water-soluble salts (hereinafter, also referred to as a component (J)). Preferably, the water-soluble salts as the component (J) are one or more selected from water-soluble organic salts other than water-soluble inorganic salts and surfactants. Examples of preferable water-soluble salts include salts of organic acids such as citric acid, malic acid, succinic acid, and lactic acid; and salts of inorganic acids such as hydrochloric acid, sulfuric acid, nitric acid, carbonic acid, and phosphoric acid. Examples of cations which form the salts include alkali metals such as sodium and potassium, or ammonium and aluminum and the like. Preferable specific examples of these salts include alkali metal salts of inorganic acids such as sodium chloride and sodium sulfate; ammonium salts of inorganic acids such as ammonium chloride, ammonium sulfate, and ammonium nitrate; alkali metal salts of organic acids (particularly, aliphatic organic acids are preferable) such as trisodium citrate; and ammonium salts of organic acids (particularly, aliphatic organic acids are preferable). Among these, alkali metal salts of inorganic acids or ammonium salts of inorganic acids are preferable from the viewpoint of a use feel when these are used for a cleansing composition for skin or hair. One or more thereof may be used.

From the viewpoint of improvement in the feel and the effect of adjusting viscosity, the content of the component (J) is preferably from 0.1 to 10% by mass, more preferably from 0.2 to 5% by mass, and even more preferably from 0.2 to 2% by mass in the cleansing composition according to the present invention. From the viewpoint of improvement in the feel and the effect of adjusting viscosity, the mass content ratio of the component (A) to the component (J) (component (A)/component (J)) is preferably from 100 to 0.1, more preferably from 50 to 1, and even more preferably from 50 to 5. At a mass ratio within this range, an effect of improving fluidity can be sufficiently demonstrated.

From the viewpoint of improving the appearance and stability of the cleansing composition, and the sterilization effect and antibacterial effect, preferably, the cleansing composition according to the present invention further contains a chelating agent (hereinafter, also referred to as a component (K)).

The chelating agent as the component (K) is not particularly limited as long as the chelating agent has an ability to chelate metal ions. Examples thereof include aminopolycarboxylic acid chelating agents, aromatic and aliphatic carboxylic acid chelating agents, amino acid chelating agents, ether polycarboxylic acid chelating agents, phosphonic acid chelating agents such as iminodimethylphosphonic acid (IDP), alkyl diphosphonic acid (ADPA), and 1-hydroxyethane-1,1-diphosphonic acid (DEQUEST (trademark) 2010), hydroxycarboxylic acid chelating agents, phosphoric acid chelating agents, polymer electrolyte (including oligomer electrolytes) chelating agents, and dimethyl glyoxime (DG). These chelating agents as the component (K) may be a free acid type or a salt type such as sodium salts, potassium salts, and ammonium salts, and further, may be an ester derivative thereof that can be hydrolyzed.

Specific examples of the aminopolycarboxylic acid chelating agents include ethylenediaminetetraacetic acid (EDTA), cyclohexanediaminetetraacetic acid (CDTA), nitrilotriacetic acid (NTA), iminodiacetic acid (IDA), N-(2-hydroxyethyl)iminodiacetic acid (HIMDA), diethylenetriaminepentaacetic acid (DTPA), N-(2-hydroxyethyl)ethylenediaminetriacetic acid (EDTA-OH) and glycoletherdiaminetetraacetic acid (GEDTA), and salts thereof.

Specific examples of the aromatic or aliphatic carboxylic acid chelating agents include oxalic acid, malonic acid, succinic acid, glutaric acid, adipic acid, itaconic acid, aconitic acid, pyruvic acid, salicylic acid, acetylsalicylic acid, hydroxybenzoic acid, aminobenzoic acid (including anthranilic acid), phthalic acid, trimellitic acid, and gallic acid, as well as salts, methyl esters, and ethyl esters thereof. Examples of the amino acid chelating agents include glycine, serine, alanine, lysine, cystine, cysteine, ethionine, tyrosine, methionine, and salts and derivatives thereof.

Further, examples of the etherpolycarboxylic acid chelating agents include diglycolic acid, compounds represented by the general formula (9) below, and analogous compounds and salts thereof (such as sodium salts):

(9)

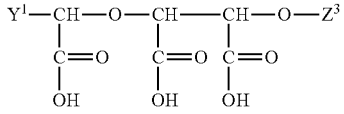

[wherein $Y^1$ represents a hydrogen atom, $—CH_2COOH$, or $—COOH$, and $Z^3$ represents a hydrogen atom, $—CH_2COOH$, or

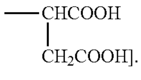

].

Specific examples of the hydroxycarboxylic acid chelating agents include malic acid, citric acid, glycolic acid, gluconic acid, heptonic acid, tartaric acid and lactic acid, and salts thereof. Examples of the phosphoric acid chelating agents include orthophosphoric acid, pyrophosphoric acid, triphosphoric acid, and polyphosphoric acid. Specific examples of the polymer electrolyte (including oligomer electrolytes) chelating agents include acrylic acid polymers, maleic anhydride polymers, α-hydroxyacrylic acid polymers, itaconic acid polymers, copolymers composed of two or more monomers which form these polymers, and epoxy succinic acid polymers. Further, ascorbic acid, thioglycolic acid, phytic acid, glyoxylic acid and glyoxal acid, and salts thereof may also be suitably used as the chelating agent of the component (K).

From the viewpoint of availability and improvement in the stability of the cleansing composition, examples of chelating agents as the component (K) include preferably ethylenediaminetetraacetic acid (EDTA), succinic acid, salicylic acid, oxalic acid, lactic acid, fumaric acid, tartaric acid and 1-hydroxyethane-1,1-diphosphonic acid, and salts thereof.

The content of the component (K) is preferably from 0.01 to 10% by mass, more preferably from 0.02 to 2% by mass, and even more preferably from 0.05 to 1% by mass in the cleansing composition according to the present invention.

Further, the cleansing composition according to the present invention may contain an anti-inflammatory agent such as glycyrrhizic acid, dihydrocholesterin, or allantoin in the range in which the effect of the present invention is not impaired.

From the viewpoint of imparting to hair combability and softness from during rinsing to after drying and manageability after drying, and imparting a moist feeling to skin, the cleansing composition according to the present invention preferably contains an oil solution (hereinafter, also referred to as a component (L)). Specific examples of the oil solution as the component (L) include ester oils, silicone oils, ether oils, hydrocarbon oils, higher alcohols, or carboxylic acids having an optionally substituted hydroxy group and a hydrocarbon group having from 17 to 23 carbon atoms.

Specific examples of the aforementioned ester oil include castor oil, cacao oil, mink oil, avocado oil, olive oil, sunflower oil, *camellia* oil, apricot kernel oil, almond oil, wheat germ oil, *theobroma grandiflorum* seed oil, grape seed oil, babassu oil, jojoba oil, macadamia nut oil, *camellia oleifera* seed oil, shea butter oil, *camellia reticulata* seed oil, meadowfoam oil, bees wax, lanolin, hydrogenated lanolin, octyldodecyl lanolate, caprylyl eicosenoate, diisopropyl dimerate, myristyl 2-ethylhexanoate, cetyl 2-ethylhexanoate, stearyl 2-ethylhexanoate, octyl octanoate, lauryl octanoate, myristyl octanoate, isocetyl octanoate, octyl propylheptanoate, cetostearyl isononanoate, isononyl isononanoate, isotridecyl isononanoate, methyl laurate, hexyl laurate, octyl laurate, isopropyl myristate, octyl myristate, myristyl myristate, octyldodecyl myristate, isopropyl palmitate, 2-ethylhexyl palmitate, octyl palmitate, cetyl palmitate, methyl oleate, oleyl oleate, decyl oleate, isobutyl oleate, methyl stearate, 2-ethylhexyl stearate, octyl stearate, isocetyl stearate, stearyl stearate, butyl stearate, isotridecyl stearate, isopropyl isostearate, isocetyl isostearate, isostearyl isostearate, propylene glycol isostearate, 2-ethylhexyl hydroxystearate, oleyl erucate, propanediol dicaprate, diisopropyl adipate, diethoxyethyl succinate, 2-ethylhexyl succinate, sucrose polysoyate, sucrose polybehenate, sucrose tetraisostearate, glyceryl tribehenate, triisostearin, and pentaerythrityl tetrastearate.

Among them, from the viewpoint of imparting good combability, softness and manageability to hair after drying treated with the cleansing composition, sunflower oil, avocado oil, *camellia* oil, macadamia nut oil, shea butter oil, octyl laurate, octyl myristate, octyldodecyl myristate, isopropyl myristate, myristyl myristate, isopropyl palmitate, 2-ethylhexyl palmitate, octyl palmitate, cetyl palmitate, methyl stearate, 2-ethylhexyl stearate, octyl stearate, isocetyl stearate, stearyl stearate, butyl stearate, and isotridecyl stearate are preferable, and one or more selected from sunflower oil, avocado oil, *camellia* oil, macadamia nut oil, shea butter oil, octyl laurate, octyl myristate, myristyl myristate, isopropyl palmitate, octyl palmitate, cetyl palmitate, octyl stearate, isocetyl stearate, stearyl stearate, isostearyl stearate, and isostearyl isostearate are more preferable.

Also, as the aforementioned ester oil, a hydrophobic carboxylic acid ester of dipentaerythritol may also be used. The hydrophobic carboxylic acid ester of dipentaerythritol refers to a compound obtained by subjecting dipentaerythritol to dehydration condensation with one or more hydrophobic carboxylic acids. Here, the hydrophobic carboxylic acid refers to a carboxylic acid having a hydrocarbon group having from 16 to 24 carbon atoms optionally having a hydroxyl group. Specific examples of the hydrophobic carboxylic acid include palmitic acid, stearic acid, oleic acid, isostearic acid, hydroxystearic acid, and rosin acid. From the viewpoint of availability, an ester of mixed acid of hydroxystearic acid, stearic acid, and rosin acid and dipentaerythritol is preferable.

From the viewpoint of imparting good manageability to hair after drying treated with the cleansing composition according to the present invention, and imparting moist feeling to skin, as the aforementioned silicone oil, one or more selected from dimethylpolysiloxane, dimethiconol (dimethylpolysiloxane having a hydroxyl group at the end), amino-modified silicone (dimethylpolysiloxane having an amino group within the molecule), polyether-modified silicone, glyceryl-modified silicone, amino derivative silicone, silicone wax, and silicone elastomer are preferable. From the viewpoint of the finger combability and the manageability of the hair, and dispersibility during preparation of the cleansing composition for skin or hair, the viscosity of the aforementioned silicone oil is preferably from 10 to 15 million $mm^2/s$.

From the viewpoint of imparting good combability, softness, and manageability to hair after drying treated with the cleansing composition according to the present invention, and imparting moist feeling to skin, examples of the aforementioned ether oil include polyoxypropylene hexyl ether, polyoxypropylene octyl ether, polyoxypropylene decyl ether, polyoxypropylene lauryl ether, dihexyl ether, dioctyl ether, didecyl ether, dilauryl ether, dimyristyl ether, dicetyl ether, distearyl ether, diicosyl ether, and dibehenyl ether in which the average number of moles of propyleneoxy groups added is 3, 7, 10 or 15. Among them, polyoxypropylene hexyl ether, polyoxypropylene octyl ether, polyoxypropylene decyl ether, polyoxypropylene lauryl ether, dioctyl ether, didecyl ether, and dilauryl ether in which the average number of moles of oxypropylene added is 3 are preferable, and one or more selected from polyoxypropylene octyl ether, polyoxypropylene decyl ether, and polyoxypropylene lauryl ether in which the average number of moles of oxypropylene added is 3 are more preferable.

From the viewpoint of combability, softness, and manageability to hair after drying treated with the cleansing composition according to the present invention, and from the viewpoint of moist feeling to skin, the aforementioned hydrocarbon oil is preferably saturated or unsaturated hydrocarbon having 20 or more carbon atoms.

Specific examples of the aforementioned hydrocarbon oil include squalene, squalane, liquid paraffin, liquid isoparaffin, heavy liquid isoparaffin, α-olefin oligomer, cycloparaffin, polybutene, petroleum jelly, paraffin wax, microcrystalline wax, polyethylene wax, or ceresin. From the viewpoint of manageability of hair, squalane, squalene, liquid paraffin, or paraffin wax is preferable, and one or more selected from squalane, liquid paraffin, and paraffin wax are more preferable.

From the viewpoint of maganeability of hair after drying treated with the cleansing composition of the present invention, the aforementioned higher alcohol is preferably an alcohol having a linear or branched alkyl group or alkenyl group having from 6 to 22 carbon atoms. The number of carbon atoms in the above alkyl group or alkenyl group is more preferably from 8 to 20, and even more preferably from 12 to 18. Specific examples of the aforementioned higher alcohol include hexyl alcohol, 2-ethylhexyl alcohol, octyl alcohol, decyl alcohol, isodecyl alcohol, lauryl alcohol, myristyl alcohol, palmityl alcohol, cetyl alcohol, stearyl alcohol, isostearyl alcohol, 2-octyl dodecanol, icosyl alcohol, or behenyl alcohol.

Among them, from the viewpoint of manageability of hair and moist feeling of skin, lauryl alcohol, myristyl alcohol, cetyl alcohol, stearyl alcohol, behenyl alcohol, or 2-octyl dodecanol is preferable, of which lauryl alcohol, myristyl alcohol, cetyl alcohol, stearyl alcohol, or 2-octyl dodecanol is more preferable, and one or more selected from cetyl alcohol, stearyl alcohol, and 2-octyl dodecanol are more preferable. The hydrocarbon group of the aforementioned carboxylic acid having a hydrocarbon group having from 17 to 23 carbon atoms which may be substituted by a hydroxyl group is preferably a linear or branched alkyl group or alkenyl group. Specific examples of the carboxylic acid having a hydrocarbon group having from 17 to 23 carbon atoms which may be substituted by a hydroxyl group include stearic acid, oleic acid, isostearic acid, hydroxystearic acid, behenic acid, or rosin acid. Among them, from the viewpoint of finger combability and manageability of hair, stearic acid, oleic acid, isostearic acid, hydroxystearic acid, or behenic acid is preferable, of which oleic acid or isostearic acid is more preferable.

From the viewpoint of imparting combability, softness, and manageability to hair after drying treated with the cleansing composition, and imparting moist feeling to skin, the solubility of the aforementioned component (L) to be used in the present invention in 100 g of water at 20° C. is preferably from 0 to 1 g, more preferably from 0 to 0.5 g, and even more preferably from 0 to 0.1 g.

From the viewpoint of imparting good combability, softness, and manageability to hair after drying treated with the cleansing composition, and imparting moist feeling to skin, the content of the aforementioned component (L) is preferably from 0.01 to 30% by mass, more preferably from 0.05 to 10% by mass, and even more preferably from 0.1 to 5% by mass. Also, from the viewpoint of improving durability of foam and rinse feel, obtaining combability after rinsing and drying, softness, and manageability of hair treated with the cleansing composition, and obtaining moist feeling to skin, the mass content ratio of the aforementioned component (A) to the aforementioned component (L), [Component (A)/Component (L)], is preferably from 0.2 to 100, more preferably from 0.5 to 100, more preferably from 1 to 50, and even more preferably from 3 to 35.

From the viewpoint of improving a good rinse feel and durability of foam, imparting softness to hair during rinsing and after towel drying, and imparting a moist feeling to skin after towel drying, the cleansing composition of the present invention preferably contains a cationic polymer or an amphoteric polymer (hereinbelow, may also be referred to as a component (M)).

From the viewpoint of finger combability and softness during rinsing of the hair according to the cleansing composition, softness after towel drying, volume of foam during washing of the skin, improvement in good rinse feel and durability of foam, and moist feeling after drying, examples of a preferable cationic polymer include cationic galactomannan, cationized hydroxyethyl cellulose, cationized hydroxypropyl cellulose, cationized starch, or a synthetic polymer synthesized by a radical polymerization.

The aforementioned cationic galactomannan is a polymer in which a cationic group is introduced into a galactomannan polysaccharide, and the cationic galactomannan is preferably a cationic polymer into which a quaternary nitrogen-containing substituent is introduced. The cationic galactomannan may be obtained by reacting a galactomannan polysaccharide with a cationizing agent.

From the viewpoint of the foaming performance by the cleansing composition, volume of foam, durability of foam, rinse feel, finger combability and softness during rinsing of the hair, softness after towel drying, volume of foam, durability of foam and good rinse feel during washing of the skin, and moist feeling after drying, examples of preferable cationic galactomannan to be used in the present invention include cationized tara gum, cationized locust bean gum, cationized *Trigonella foenum-graecum* gum, cationized guar gum, cationized *cassia* gum, cationized fenugreek gum, cationized honey locust gum, or cationized *Brachychiton acerifolium*. Among them, from the viewpoint of the finger combability by the cleansing composition and softness during rinsing of the hair, softness after towel drying, volume of foam, good rinse feel and durability of foam during washing the skin, and a moist feeling after drying, cationized tara gum, cationized locust bean gum, cationized guar gum, cationized *cassia* gum, or cationized fenugreek gum are more preferable.

Examples of a commercial product of the aforementioned cationized tara gum include CATINAL CTR-100 (the product of Toho Chemical Industry Co., Ltd.). Examples of a commercial product of the aforementioned cationized locust bean gum include CATINAL CLB-100 (the product of Toho Chemical Industry Co., Ltd.). Examples of a commercial product of the cationized *Trigonella foenum-graecum* gum include CATINAL CG-100 (the product of Toho Chemical Industry Co., Ltd.). Examples of a commercial product of the cationized guar gum include JAGUAR C-13S, JAGUAR C-14S, JAGUAR C-17, JAGUAR C-500, JAGUAR C-162, and JAGUAR EXCEL, all of which are sold by Rhodia, and N-Hance BF17, N-Hance 3215, N-Hance CCG450, N-Hance 3196, N-Hance BF13, N-Hance CG13, N-Hance CCG45, N-Hance 3000, AquaCat PF618, AquaCat CG518, and N-Hance HPCG1000, all of which are sold by Ashland Inc. Examples of a commercial product of the cationized cassia gum include Sensomer CT-250 polymer and Sensomer ST-400 polymer, both of which are sold by The Lubrizol Corporation.

In the present invention, cationized hydroxyethyl cellulose (hereinbelow, may also be referred to as "C-HEC") refers to cellulose having a cationic group and an ethyleneoxy group. C-HEC is obtained by adding a cationic group and an ethyleneoxy group to cellulose. As the cationic group, a quaternary ammonium group is preferable.

Examples of a commercial product of C-HEC include UCARE JR125, UCARE JR400, UCARE JR30M, UCARE LR400, UCARE LR30M, SOFTCAT SL-5, SOFTCAT SL-30, SOFTCAT SL-60, SOFTCAT SL-100, SOFTCAT SX-400X, SOFTCAT SX-1300H, SOFTCAT SX-1300X, SOFTCAT SK-H, and SOFTCAT SK-MH, all of which are sold by The Dow Chemical Company.

In the present invention, cationized hydroxypropyl cellulose (hereinbelow, may also be referred to as "C-HPC") refers to cellulose having a cationic group and a propyleneoxy group. The cationized hydroxypropyl cellulose is obtained by reacting a cationizing agent and propylene oxide with cellulose.

Aforementioned cationized starch refers to starch into which a quaternary nitrogen-containing substituent is introduced. The cationized starch is obtained by reacting a cationizing agent with starch. As a cationic group, a quaternary ammonium group is preferable. Examples of a commercial product of cationized starch include Sensomer CI-50, which is sold by The Lubrizol Corporation.

A synthetic polymer may be used as the component (M). Examples of a preferable synthetic polymer to be used in the present invention include a methacryloxyalkyl quaternary ammonium salt/acrylamide copolymer, a diallyl quaternary ammonium salt/acrylamide copolymer, a diallyl quaternary ammonium salt/acrylic acid copolymer, a diallyl quaternary ammonium salt/acrylamide/acrylic acid copolymer, a methacrylamide alkyl quaternary ammonium salt/acrylic acid/acrylic acid ester copolymer, a methacrylamide alkyl quaternary ammonium salt/acrylic acid/acrylamide copolymer, or a diallyl quaternary ammonium salt/vinylpyrrolidone/vinylimidazole copolymer.

Among those polymer, from the viewpoint of foaming performance by the cleansing composition, volume of foam, durability of foam, rinse feel, finger combability and softness during rinsing of the hair, softness after towel drying, volume of foam, durability of foam and good rinse feel during washing of the skin, and moist feeling after drying, the polymer is more preferably a diallyl quaternary ammonium salt/acrylamide/acrylic acid copolymer, a methacrylamide alkyl quaternary ammonium salt/acrylic acid/acrylic acid ester copolymer, a methacrylamide alkyl quaternary ammonium salt/acrylic acid/acrylamide copolymer, or a diallyl quaternary ammonium salt/vinylpyrrolidone/vinylimidazole copolymer.

Examples of a commercial product of the aforementioned methacryloxyalkyl quaternary ammonium salt/acrylamide copolymer include Merquat (trademark) 5 (the product of The Lubrizol Corporation). Examples of a commercial product of the diallyl quaternary ammonium salt/acrylamide copolymer include Merquat (trademark) 550, Merquat (trademark) 740, Merquat (trademark) 2200, and Merquat (trademark) S (all are the products of The Lubrizol Corporation). Examples of a commercial product of the diallyl quaternary ammonium salt/acrylic acid copolymer include Merquat (trademark) 280 and Merquat (trademark) 295 (both are the products of The Lubrizol Corporation). Examples of a commercial product of the diallyl quaternary ammonium salt/acrylamide/acrylic acid copolymer include Merquat (trademark) 3330 DRY (the product of The Lubrizol Corporation). Examples of a commercial product of the methacrylamide alkyl quaternary ammonium salt/acrylic acid/acrylic acid ester copolymer include Merquat (trademark) 2001 (the product of The Lubrizol Corporation). Examples of a commercial product of the methacrylamide alkyl quaternary ammonium salt/acrylic acid/acrylamide copolymer include Merquat (trademark) 2003 (the product of The Lubrizol Corporation). Examples of a commercial product of the diallyl quaternary ammonium salt/vinylpyrrolidone/vinyl imidazole copolymer include Luviquat (trademark) Sensation, which is manufactured and sold by BASF.

From the viewpoint of the foaming performance of the cleansing composition, volume of foam, durability of foam, rinse feel, finger combability and softness during rinsing of the hair, softness after towel drying, volume of foam, durability of foam and good rinse feel, during washing of the skin, and moist feeling after drying, the content of the component (M) is preferably from 0.01 to 5% by mass, more preferably from 0.05 to 1% by mass, and even more preferably from 0.1 to 0.5% by mass in the cleansing composition according to the present invention. From the viewpoint of the foaming performance of the cleansing composition, volume of foam, durability of foam, rinse feel, finger combability and softness during rinsing of the hair, softness after towel drying, volume of foam, durability of foam and good rinse feel during washing of the skin, and moist feeling after drying, the mass content ratio of the component (A) to the component (M) [component (A)/component (M)] is preferably from 5 to 250, more preferably from 10 to 100, and even more preferably from 20 to 50 in the cleansing composition according to the present invention.

<Other Components>

In the cleansing composition according to the present invention, a non-reacted raw material internal olefin may remain because of the production step of the component (A). The content of the raw material internal olefin in the cleansing composition according to the present invention is preferably 2.0% by mass or less, more preferably 1.0% by mass or less, more preferably 0.5% by mass or less, and even more preferably 0.2% by mass or less from the viewpoint of the volume of foam, a lathering speed, and rinse feel. The content of the raw material internal olefin in the cleansing composition according to the present invention is preferably 0.0001% by mass or more, more preferably 0.001% by mass or more, and even more preferably 0.01% by mass or more. The content of the non-reacted raw material internal olefin in the cleansing composition according to the present invention may be measured in accordance with the method described in Examples.

The raw material internal olefin used in production of the component (A) may contain a paraffin component. In this case, the paraffin component is contained in the cleansing composition according to the present invention. The content of the paraffin component is preferably 10% by mass or less, more preferably 5% by mass or less, even more preferably 3% by mass or less in the raw material internal olefin from the viewpoint of lathering property, and preferably 0.001% by mass or more in the raw material internal olefin from the viewpoint of cost reduction and improvement in productivity. The content of the paraffin component may be measured by GC-MS, for example. Specifically, the content may be determined in accordance with the method described in Examples.

The cleansing composition of the present invention may contain, in addition to the aforementioned components, water, which may serve as a medium of the component (A), a viscosity reducing agent, polyhydric alcohols, a preservative, and a reducing agent, and also, other components used as ordinary cosmetic raw materials. Examples of other components usually used as a cosmetic raw material include a feel improver, an ultraviolet absorber, a visible light absorber, an antioxidant, a colorant, a preservative, a pH adjuster, and a viscosity regulator and the like.

<Production Method of the Cleansing Composition of the Present Invention>

No particular limitation is imposed on the production method of the cleansing composition of the present invention, and it may be produced by a conventional method. Specifically, for example, in the case of a liquid shampoo for hair, water and an internal olefin sulfonate (A) are heated and mixed to homogeneity. If necessary, the internal olefin sulfonate (A) may be dispersed or dissolved in water in advance, and then added. The cleansing composition of the present invention may also be prepared by adding the internal olefin sulfonate (A) to an aqueous solution of a surfactant and homogeneously dissolving or dispersing it, followed by cooling, and if necessary, adding the aforementioned components from (B) to (M), a pH adjuster, a dye, and the like.

No particular limitation is imposed on the form of the cleansing composition of the present invention, and it may be provided in any form such as a liquid, a foam, a paste, a cream, a solid, and a powder, among which a liquid, a paste, or a cream is preferable, and a liquid is more preferable. When the cleansing composition is provided as a liquid, polyethylene glycol, ethanol, and the like are preferably used as a liquid medium in addition to water. The content of water in the cleansing composition of the present invention is preferably 10% by mass or more and 90% by mass or less.

<Intended Use and Method of Use>

The cleansing composition of the present invention can impart a good durability of foam and rinse feel, combability and softness after rinsing, and softness and manageability after drying to hair, and a moist feeling to skin; therefore, it can be preferably used as a cleansing composition for hair or a cleansing composition for skin. Examples of the cleansing composition for hair include a hair shampoo. Examples of the cleansing composition for skin include a body shampoo, a facial cleanser, a makeup remover, or a hand soap.

Because the cleansing composition of the present invention can impart a good durability of foam and rinse feel, combability and softness after rinsing, and softness and manageability after drying to hair, and a moist feeling to skin, a method for washing the hair which includes applying the aforementioned cleansing composition of the present invention to hair, followed by washing and then rinsing is also provided. Also, a method for washing the body which includes applying the aforementioned cleansing composition of the present invention to a surface of the skin, followed by washing and then rinsing is also provided.

Hereinafter, with reference to the above-mentioned embodiment, the present invention will disclose the following cleansing composition for skin or hair.

[1] A cleansing composition for skin or hair comprising an internal olefin sulfonate (A) having 12 or more and 24 or less carbon atoms.

[2] The cleansing composition for skin or hair of above [1], in which the number of carbon atoms in the internal olefin sulfonate is preferably 14 or more, more preferably 16 or more, and preferably 20 or less, more preferably 18 or less.

[3] The cleansing composition for skin or hair of above [1] or [2], in which the mass content ratio of the internal olefin sulfonate having 16 carbon atoms to the internal olefin sulfonate having 18 carbon atoms in the component (A) (internal olefin sulfonate having 16 carbon atoms/internal olefin sulfonate having 18 carbon atoms) is preferably from 50/50 to 99/1, more preferably from 60/40 to 95/5, more preferably from 70/30 to 90/10, more preferably from 75/25 to 90/10, more preferably from 75/25 to 85/15, and even more preferably from 78/22 to 85/15.

[4] The cleansing composition for skin or hair of any one of above [1] to [3], in which a total content of the internal olefin sulfonate having 16 carbon atoms and the internal olefin sulfonate having 18 carbon atoms in the component (A) is preferably 50% by mass or more, more preferably 60% by mass, more preferably 70% by mass, more preferably 80% by mass or more, more preferably 90% by mass or more, and even more preferably 95% by mass or more.

[5] The cleansing composition for skin or hair of any one of above [1] to [4], in which a content of an internal olefin sulfonate in which a sulfonate group is present at a C-2 position in the component (A) is preferably 25% by mass or less, more preferably 24% by mass or less, more preferably 23% by mass or less, more preferably 22% by mass or less, more preferably 20% by mass or less, more preferably less than 20% by mass, more preferably 19% by mass or less, and even more preferably 18% by mass or less.

[6] The cleansing composition for skin or hair of any one of above [1] to [5], in which a content of an internal olefin sulfonate in which a sulfonate group is present at a C-2 position in the component (A) is preferably 5% by mass or more and 25% by mass or less, more preferably 5% by mass or more and 24% by mass or less, more preferably 5% by mass or more and 23% by mass or less, more preferably 5% by mass or more and 22% by mass or less, preferably 5% by mass or more and 20% by mass or less, more preferably 6% by mass or more and less than 20% by mass, more preferably 7% by mass or more and 19% by mass or less, and even more preferably 8% by mass or more and 18% by mass or less.

[7] The cleansing composition for skin or hair of any one of above [1] to [6], in which a content of the internal olefin sulfonate in which a sulfonate group is present at the C-2 position in the component (A) is preferably 9% by mass or more and 17.5% by mass or less, more preferably 9% by mass or more and 15% by mass or less, more preferably 9% by mass or more and 12% by mass or less, and even more preferably 9% by mass or more and 10% by mass or less.

[8] The cleansing composition for skin or hair of any one of above [1] to [7], in which a content of the internal olefin sulfonate in which a sulfonate group is present at the C-2 position in the component (A) is preferably 9% by mass or more and 18% by mass or less, more preferably 10% by mass or more and 18% by mass or less, more preferably 12% by mass or more and 18% by mass or less, more preferably 14% by mass or more and 18% by mass or less, and even more preferably 16% by mass or more and 18% by mass or less.

[9] The cleansing composition for skin or hair of any one of above [1] to [8], in which a content of an internal olefin sulfonate in which a sulfonate group is present at a C-2 position in the component (A) is preferably 5% by mass or more, more preferably 6% by mass or more, more preferably 7% by mass or more, more preferably 8% by mass or more, more preferably 9% by mass or more, more preferably 10% by mass or more, more preferably 12% by mass or more, more preferably 14% by mass or more, and even more preferably 16% by mass or more.

[10] The cleansing composition for skin or hair of any one of above [1] to [9], in which a content of an internal olefin sulfonate in which a sulfonate group is present at a C-2 position in the component (A) is preferably 20% by mass or less, more preferably less than 20% by mass, more preferably 19% by mass or less, more preferably less than 18% by mass, even more preferably 17.5% by mass or less, and preferably 5% by mass or more, more preferably 6% by mass or more, more preferably 7% by mass or more, more preferably 8% by mass or more, and even more preferably 9% by mass or more.

[11] The cleansing composition for skin or hair of any one of above [1] to [10], in which the content of an internal olefin sulfonate in which the sulfonate group is present at the C-1 position of the olefin chain or alkane chain in the component (A) is preferably 3.0% by mass or less, more preferably 2.5% by mass or less, more preferably 2.0% by mass or less, more preferably 1.5% by mass or less, and even more preferably 1.0% by mass or less, and more preferably 0.01% by mass or more.

[12] The cleansing composition for skin or hair of any one of above [1] to [11], in which the mass content ratio (hydroxy form/olefin form) of the hydroxy form of an internal olefin sulfonate to the olefin form of an internal olefin sulfonate in the component (A) is preferably from 50/50 to 100/0, more preferably from 60/40 to 100/0, more preferably from 70/30 to 100/0, more preferably from 75/25 to 100/0, and even more preferably from 75/25 to 95/5.

[13] The cleansing composition for skin or hair of any one of above [1] to [12], in which when the component (A) is obtained by a sulfonation of the raw material internal olefin, followed by neutralization and then hydrolysis, the content of an internal olefin in which the double bond is present at the C-2 position in the raw material internal olefin is preferably 40% by mass or less, more preferably 35% by mass or less, more preferably 32% by mass or less, and even more preferably 30% by mass or less, and preferably 5% by mass or more, more preferably 6% by mass or more, more preferably 7% by mass or more, more preferably 8% by mass or more, more preferably 9% by mass or more, more preferably 12% by mass or more, and even more preferably 15% by mass or more.

[14] The cleansing composition for skin or hair of any one of above [1] to [13], in which when the component (A) is obtained by a sulfonation of the raw material internal olefin, followed by neutralization and then hydrolysis, a content of the internal olefin in which the double bond is present at a C-2 position in the raw material internal olefin is preferably 5% by mass or more and 40% by mass or less, more preferably 5% by mass or more and 35% by mass or less, more preferably 5% by mass or more and 32% by mass or less, more preferably 5% by mass or more and 30% by mass or less, preferably 6% by mass or more and 30% by mass or less, more preferably 7% by mass or more and 30% by mass or less, more preferably 8% by mass or more and 30% by mass or less, more preferably 9% by mass or more and 30% by mass or less, more preferably 12% by mass or more and 30% by mass or less, and even more preferably 15% by mass or more and 27% by mass or less.

[15] The cleansing composition for skin or hair of any one of above [1] to [14], in which when the component (A) is obtained by a sulfonation of the raw material internal olefin, followed by neutralization and then hydrolysis, a content of the internal olefin in which the double bond is present at a C-2 position in the raw material internal olefin is preferably 15% by mass or more and 25% by mass or less, more preferably 15% by mass or more and 20% by mass or less, more preferably 15% by mass or more and less than 20% by mass, more preferably 15% by mass or more and 19% by mass or less, and even more preferably 15% by mass or more and 18% by mass or less.

[16] The cleansing composition for skin or hair of any one of above [1] to [15], in which when the component (A) is obtained by a sulfonation of the raw material internal olefin, followed by neutralization and then hydrolysis, a content of the internal olefin in which the double bond is present at a C-2 position in the raw material internal olefin is preferably 20% by mass or more and 27% by mass or less, more preferably 22% by mass or more and 27% by mass or less, and even more preferably 24% by mass or more and 27% by mass or less.

[17] The cleansing composition for skin or hair of any one of above [1] to [16], in which the content of the component (A) in the cleansing composition is preferably 0.1% by mass or more, more preferably 1% by mass or more, more preferably 2% by mass or more, and even more preferably 5% by mass or more, and preferably 80% by mass or less, more preferably 50% by mass or less, more preferably 30% by mass or less, and even more preferably 20% by mass or less.

[18] The cleansing composition for skin or hair of any one of above [1] to [17], in which a content of the raw material internal olefin in the component (A) is preferably less than 5.0% by mass, more preferably less than 3.0% by mass, more preferably less than 1.5% by mass, and even more preferably less than 1.0% by mass in the component (A).

[19] The cleansing composition for skin or hair of any one of above [1] to [18], in which a content of the inorganic compounds in the component (A) is preferably less than 7.5% by mass, more preferably less than 5.0% by mass, more preferably less than 3.0% by mass, more preferably less than 2.0% by mass, and even more preferably less than 1.6% by mass in the component (A).

[20] The cleansing composition for skin or hair of any one of above [1] to [19], which further comprises a surfactant (B) other than the component (A).

[21] The cleansing composition for skin or hair of above [20], in which the component (B) preferably includes an anionic surfactant, a nonionic surfactant, or an amphoteric surfactant other than the component (A).

[22] The cleansing composition for skin or hair of above [20] or [21], in which a content of the component (B) is preferably 50% by mass or less, more preferably 30% by mass or less, more preferably 20% by mass or less, more preferably 15% by mass or less, more preferably 10% by mass or less, and preferably 0.1% by mass or more, more preferably 0.5% by mass or more, and even more preferably 1.0% by mass or more.

[23] The cleansing composition for skin or hair of any one of above [1] to [22], which further comprises a moisturizing agent (C).

[24] The cleansing composition for skin or hair of [23], in which the component (C) is preferably one or more selected from ceramides, plant extracts, sodium hyaluronate, propylene glycol, 1,3-butylene glycol, glycerol and derivatives thereof, sorbitol and derivatives thereof, sodium lactate, sodium pyrrolidonecarboxylate, carbitol, diethylene glycol monomethyl ether, sugar alcohols (such as maltitol, xylitol, sorbitol, erythritol, and lactitol), medium-chain fatty acid triglycerides, and urea, more preferably ceramides, plant extracts, sodium hyaluronate, and glycerol and derivatives thereof.

[25] The cleansing composition for skin or hair of above [23] or [24], in which the mass content ratio of the component (A) to the component (C) [component (A)/component (C)] is preferably from 500 to 0.01, more preferably from 200 to 0.1, more preferably from 50 to 5, and a content of the component (C) is preferably from 0.001 to 30% by mass, more preferably from 0.01 to 5% by mass.

[26] The cleansing composition for skin or hair of any one of above [1] to [25], which further comprises an antibacterial agent or an anti-dandruff agent (D).

[27] The cleansing composition for skin or hair of [26], in which the antibacterial agent is preferably one or two or more selected from triclosan, triclocarban, piroctone olamine, zinc pyrithione, selenium disulfide, and 3-methyl-4-(1-methylethyl)phenol.

[28] The cleansing composition for skin or hair of above [26] or [27], in which the content of the component (D) to be blended is preferably from 0.005 to 5% by mass, more preferably from 0.01 to 3% by mass, and even more preferably from 0.05 to 2% by mass.

[29] The cleansing composition for skin or hair of any one of above [1] to [28], which further comprises a pearling agent (E).

[30] The cleansing composition for skin or hair of above [29], in which the component (E) is preferably one or two or more selected from ethylene glycol distearate, ethylene glycol monostearate, diethylene glycol distearate, ethylene glycol dipalmitate, and distearyl ether.

[31] The cleansing composition for skin or hair of above [29] or [30], in which the content of the component (E) is preferably not less than 0.3% by mass and not more than 10% by mass, more preferably not less than 0.5 and not more than 5.0% by mass, and even more preferably not less than 1.0 and not more than 2.0% by mass.

[32] The cleansing composition for skin or hair of any one of above [1] to [31], which further comprises a fragrance (F).

[33] The cleansing composition for skin or hair of above [32], in which the component (F) is preferably one or two or more selected from the group consisting of citrus fragrances (F1), floral fragrances (F2), woody fragrances (F3), fruity fragrances (F4), spicy fragrances (F5), musk fragrances (F6), green fragrances (F7) and others (F8).

[34] The cleansing composition for skin or hair of above [32] or [33], in which the mass content ratio of the component (A) to the component (F) [component (A)/component (F)] is preferably from 150 to 0.5, more preferably from 40 to 5, and even more preferably from 10 to 1.

[35] The cleansing composition for skin or hair of any one of above [1] to [34], which further comprises an organic solvent (G).

[36] The cleansing composition for skin or hair of above [35], in which the component (G) preferably includes aromatic alcohols, carbonates, or a hydroxy compound represented by the general formula (8) below:

$$HO \leftarrow AO \rightarrow_r R^{18} \quad (8)$$

(wherein $R^{18}$ represents a hydrogen atom or an linear or branched alkyl group or alkenyl group having from 1 to 4 carbon atoms; A represents an alkylene group having from 2 to 4 carbon atoms; the average number r of moles added represents the number of from 1 to 3000, the r number of A's may be the same or different, and A's have any disposition).

[37] The cleansing composition for skin or hair of above [35] or [36], in which the content of the component (G) is preferably from 0.1 to 30% by mass, more preferably from 0.2 to 10% by mass, and even more preferably from 0.3 to 2% by mass.

[38] The cleansing composition for skin or hair of any one of above [1] to [37], in which further comprises a vitamin agent (H).

[39] The cleansing composition for skin or hair of above [38], in which the component (H) preferably includes retinol, retinol palmitate, β-carotene, pyridoxine hydrochloride (vitamin B6), nicotinic acid amide, γ-oryzanol, riboflavin (vitamin B2), ascorbic acid (vitamin C), dl-tocopherol (vitamin E), tocopherol acetate, pantothenic acid ethyl ether, D-pantothenyl alcohol (D-panthenol) or biotin.

[40] The cleansing composition for skin or hair of above [38] or [39], in which the content of the component (H) is preferably from 0.01 to 10% by mass, more preferably from 0.05 to 5% by mass, and even more preferably from 0.1 to 1% by mass.

[41] The cleansing composition for skin or hair of any one of above [1] to [40], which further comprises a thickener (I).

[42] The cleansing composition for skin or hair of above [41], in which the component (I) preferably includes guar gum, locust bean gum, quince seed gum, carrageenan, galactan, gum arabic, tragacanth gum, pectin, mannan, starch, xanthan gum, dextran, succionoglucan, curdlan, hyaluronic acid, gelatin, casein, albumin, collagen, shellac, methyl cellulose, ethyl cellulose, hydroxyethyl cellulose, hydroxypropyl cellulose, carboxymethyl cellulose, methyl hydroxypropyl cellulose, soluble starch, carboxymethyl starch, methyl starch, hydroxypropyl starch, alginic acid propylene glycol ester, alginic acid salt, polyvinyl alcohol, polyvinylpyrrolidone, polyvinyl methyl ether, carboxyvinyl polymers, sodium polyacrylate, polyvinyl methacrylate, polyethylene oxide, ethylene oxide.propylene oxide block copolymers, polyglycol-polyamine condensates, polymethyl methacrylate fine particles, bentonite, laponite, fine powder of silicon oxide, colloidal alumina or VEEGUM.

[43] The cleansing composition for skin or hair of above [41] or [42], in which the content of the component (I) is preferably from 0.01 to 10% by mass, more preferably from 0.05 to 5% by mass, and even more preferably from 0.1 to 3% by mass.

[44] The cleansing composition for skin or hair of any one of above [1] to [43], which further comprises water-soluble salts (T).

[45] The cleansing composition for skin or hair of above [44], in which the component (J) preferably includes salts of organic acids selected from citric acid, malic acid, succinic acid and lactic acid; or salts of inorganic acids selected from hydrochloric acid, sulfuric acid, nitric acid, carbonic acid, and phosphoric acid.

[46] The cleansing composition for skin or hair of above [44] or [45], in which the content of the component (J) is preferably from 0.1 to 10% by mass, more preferably from 0.2 to 5% by mass, and even more preferably from 0.2 to 2% by mass.

[47] The cleansing composition for skin or hair of any one of above [1] to [46], which further comprises a chelating agent (K).

[48] The cleansing composition for skin or hair of above [47], in which the component (K) preferably includes aminopolycarboxylic acid chelating agents, aromatic and aliphatic carboxylic acid chelating agents, amino acid chelating agents, ether polycarboxylic acid chelating agents, phosphonic acid chelating agents such as iminodimethylphosphonic acid (IDP), alkyl diphosphonic acid (ADPA), and 1-hydroxyethane-1,1-diphosphonic acid (DEQUEST (trademark) 2010), hydroxycarboxylic acid chelating agents, phosphoric acid chelating agents, polymer electrolyte (including oligomer electrolytes) chelating agents, and dimethyl glyoxime (DG).

[49] The cleansing composition for skin or hair of above [47] or [48], in which the content of the component (K) is preferably from 0.01 to 10% by mass, more preferably from 0.02 to 2% by mass, and even more preferably from 0.05 to 1% by mass.

[50] The cleansing composition for skin or hair of any one of above [1] to [49], which further comprises an oil solution (L).

[51] The cleansing composition for skin or hair of above [50], in which the component (L) preferably includes ester oils, silicone oils, ether oils, hydrocarbon oils, higher alcohols, or carboxylic acids having an optionally substituted hydroxy group and a hydrocarbon group having from 17 to 23 carbon atoms.

[52] The cleansing composition for skin or hair of above [50] or [51], in which the content of the component (L) is preferably from 0.01 to 30% by mass, more preferably from 0.05 to 10% by mass, and even more preferably from 0.1 to 5% by mass.

[53] The cleansing composition for skin or hair of any one of above [1] to [52], which further comprises a cationic polymer or an amphoteric polymer (M).

[54] The cleansing composition for skin or hair of above [53], in which the cationic polymer preferably includes cationic galactomannan, cationized hydroxyethyl cellulose, cationized hydroxypropyl cellulose, cationized starch, or a synthetic polymer synthesized by a radical polymerization.

[55] The cleansing composition for skin or hair of above [53] or [54], in which the content of the component (M) is preferably from 0.01 to 5% by mass, more preferably from 0.05 to 1% by mass, and even more preferably from 0.1 to 0.5% by mass.

[56] A method for washing hair, comprising applying the cleansing composition for skin or hair of any one of above [1] to [55] to hair, followed by washing and then rinsing.

[57] A method for washing skin, comprising applying the cleansing composition for skin or hair of any one of above [1] to [55] to skin, followed by washing and then rinsing.

[58] A method for providing combability, softness or manageability to hair, comprising applying the cleansing composition for skin or hair of any one of above [1] to [55] to hair.

[59] A method for providing a moist feeling to skin, comprising applying the cleansing composition for skin or hair of any one of above [1] to [55] to skin.

[60] The cleansing composition for skin or hair of any one of above [1] to [55] for washing hair.

[61] The cleansing composition for skin or hair of any one of above [1] to [55] for washing skin.

[62] Use of the cleansing composition for skin or hair of any one of above [1] to [55] for washing hair.

[63] Use of the cleansing composition for skin or hair of any one of above [1] to [55] for washing skin.

[64] The cleansing composition for skin or hair of any one of above [1] to [55] for providing combability, softness or manageability to hair.

[65] The cleansing composition for skin or hair of any one of above [1] to [55] for providing a moist feeling to skin.

[66] Use of the cleansing composition for skin or hair of any one of above [1] to [55] for providing combability, softness or manageability to hair.

[67] Use of the cleansing composition for skin or hair of any one of above [1] to [55] for providing a moist feeling to skin.

[68] The cleansing composition for skin or hair of any one of above [1] to [55] for improving durability of foam.

[69] The cleansing composition for skin or hair of any one of above [1] to [55] for improving rinse feel.

EXAMPLES

Hereinbelow, the present invention will be specifically described with reference to Examples. It should be noted that unless otherwise specifically noted, "part" means "part by mass" and "%" means "% by mass" in the following Examples and Comparative Examples. Also, the methods used for measuring various physical property are as follows.

(1) Conditions of Measurement (i) Method for Measuring the Position of a Double Bond in the Internal Olefin The position of a double bond in a raw material internal olefin was measured by gas chromatography (hereinbelow, abbreviated as GC). Specifically, an internal olefin was converted to a dithiated derivative by reaction with dimethyl disulfide, and each component was separated by GC. As a result, the position of a double bond in an internal olefin was found based on the peak area of each component.

The apparatus and analytical conditions used for the measurement are as follows. GC apparatus (trade name: HP6890, the product of Hewlett-Packard Company); Column (trade name: Ultra-Alloy-1HT capillary column, 30 m×250 μm×0.15 μm, the product of Frontier Laboratories Ltd.); Detector (flame ionization detector (FID)); Injection temperature of 300° C.; Detector temperature of 350° C.; and He flow rate of 4.6 mL/minute.

(ii) Method for Measuring the Mass Ratio of Hydroxy Form/Olefin Form

The mass ratio of hydroxy form/olefin form of the internal olefin sulfonate was measured by HPLC-MS. Specifically, the hydroxy form and the olefin form were separated by HPLC and each form was identified by separately analyzing with MS. As a result, from the resulting HPLC-MS peak area, the fraction of each form was obtained.

The apparatus and analytical conditions used for the measurement are as follows. HPLC apparatus (trade name: Agilent technology 1100, the product of Agilent Technologies, Inc.); Column (trade name: L-column ODS 4.6×150 mm, the product of Chemicals Evaluation and Research Institute, Japan); Sample preparation (diluted 1000-fold with methanol); Eluent A (10 mM ammonium acetate in water); Eluent B (10 mM ammonium acetate in methanol), Gradient (0 minute (A/B=30/70%)→10 minutes (30/70%)→55 minutes (0/100%)→65 minutes (0/100%)→66 minutes (30/70%)→75 minutes (30/70%); MS apparatus (trade name: Agilent technology 1100 MS SL (G1946D); and MS detection (anion detection m/z 60-1600, UV 240 nm)

(iii) Method for Measuring the Content of the Raw Material Internal Olefin

The content of the raw material internal olefin of the internal olefin sulfonate was measured by GC. Specifically, ethanol and petroleum ether were added to an aqueous solution of internal olefin sulfonate, followed by extraction to give olefin in the petroleum ether phase. As a result, from the GC peak area of the olefin, the amount thereof was quantitated. The apparatus and analytical conditions used for the measurement are as follows. GC apparatus (trade name: Agilent technology 6850, the product of Agilent Technologies, Inc.); Column (trade name: Ultra-Alloy-1HT capillary column, 15 m×250 μm×0.15 μm, the product of Frontier Laboratories, Ltd.); Detector (flame ionization detector (FID)); Injection temperature of 300° C.; Detector temperature of 350° C.; and He flow rate of 3.8 mL/minute.

(iv) Method for Measuring the Content of Inorganic Compounds

The content of inorganic compounds was measured by potentiometric titration and neutralization titration. Specifically, the content of $Na_2SO_4$ was quantitated by measuring sulfate ion ($SO_4^{2-}$) by potentiometric titration. Also, the content of NaOH was quantitated by neutralization titration with diluted hydrochloric acid.

(v) Method for Measuring the Content of the Paraffin Component

The content of the paraffin component was measured by GC. Specifically, ethanol and petroleum ether were added to an aqueous solution of internal olefin sulfonate, followed by extraction to give paraffin in the petroleum ether phase. As a result, from the GC peak area of the paraffin, the amount thereof was quantitated. It should be noted that the apparatus and analytical conditions used for measurement are the same as those used for the measurement of the content of the raw material internal olefin.

(vi) Method for Measuring the Content of Internal Olefin Sulfonate in which a Sulfonate Group is Present at a C-2 Position The linkage position of the sulfonate group was measured by GC. Specifically, the resulting internal olefin sulfonate (A) was reacted with trimethylsilyldiazomethane to form a methyl-esterified derivative. Then, each component was separated by GC. Each of a peak area was regarded as a mass ratio, and the content of internal olefin sulfonate in which a sulfonate group is present at a C-2 position was quantitated.

The apparatus and analytical conditions used for the measurement are as follows. GC apparatus (trade name: Agilent technology 6850, the product of Agilent Technologies, Inc.); Column (trade name: HP-1 capillary column, 30 m×320 μm×0.25 μm, the product of Agilent Technologies, Inc.); Detector (hydrogen flame ionization detector (FID)); Injection temperature of 300° C.; Detector temperature of 300° C.; He flow rate of 1.0 mL/min.; oven (60° C. (0 min.)→10° C./min.→300° C. (10 min.)).

(2) Production of an Internal Olefin

Production Example A

Into a flask with a stirrer, 7000 g (25.9 moles) of 1-octadecanol (trade name: KALCOL 8098, the product of Kao Corporation), and as a solid acid catalyst, 1050 g (15 wt % relative to the raw material alcohol) of γ-alumina (STREM Chemicals, Inc.) were placed, and reactions were allowed to proceed for 13 hours at 285° C. while stirring and passing nitrogen (7000 mL/min.) through the system. The alcohol conversion ratio was 100% and the purity of C18 internal olefin was 98.5% after the completion of the reaction. The resulting crude internal olefin was transferred to a distillation flask and distilled at from 148 to 158° C./0.5 mmHg, whereby 100% pure internal olefin having 18 carbon atoms was obtained. The double bond distribution in the resulting internal olefin was 0.7% by mass at C-1 position, 16.9% by mass at C-2 position, 15.9% by mass at C-3 position, 16.0% by mass at C-4 position, 14.7% by mass at C-5 position, 11.2% by mass at C-6 position, 10.2% by mass at C-7 position, and 14.6% by mass in total at C-8 and 9 positions.

Production Example B

Into a flask with a stirrer, 7000 g (28.9 moles) of 1-hexadecanol (trade name: KALCOL 6098, the product of Kao Corporation), and as a solid acid catalyst, 700 g (10% by mass relative to the raw material alcohol) of γ-alumina (STREM Chemicals, Inc.) were placed, and reactions were allowed to proceed for five hours at 280° C. while stirring and passing nitrogen (7000 mL/minute) through the system. The alcohol conversion ratio was 100%, and the purity of C16 internal olefin was 99.7% after the completion of the reaction. The resulting crude internal olefin was transferred to a distillation flask and distilled at from 136 to 160° C./4.0 mmHg, whereby 100% pure internal olefin having 16 carbon atoms was obtained. The double bond distribution in the resulting internal olefin was 0.5% by mass at C-1 position, 16.5% by mass at C-2 position, 15.4% by mass at C-3 position, 16.4% by mass at C-4 position, 17.2% by mass at C-5 position, 14.2% by mass at C-6 position, and 19.8% by mass in total at C-7 and 8 positions.

Production Example C

Into a flask with a stirrer, 7000 g (28.9 moles) of 1-hexadecanol (trade name: KALCOL 6098, the product of Kao Corporation), and as a solid acid catalyst, 700 g (10 wt % relative to the raw material alcohol) of γ-alumina (STREM Chemicals, Inc.) were placed, and reactions were allowed to proceed for three hours at 280° C. while stirring and passing nitrogen (7000 mL/minute) through the system. The alcohol conversion ratio was 100% and the purity of C16 internal olefin was 99.6% after the completion of the reaction. The resulting crude internal olefin was transferred to a distillation flask and distilled at from 136 to 160° C./4.0 mmHg, whereby 100% pure internal olefin having 16 carbon atoms was obtained. The double bond distribution in the resulting internal olefin was 1.8% by mass at C-1 position, 30.4% by mass at C-2 position, 23.9% by mass at C-3 position, 16.8% by mass at C-4 position, 12.0% by mass at C-5 position, 7.4% by mass at C-6 position, and 7.8% by mass in total at C-7 and 8 positions.

Production Example D

Into a flask with a stirrer, 7000 g (25.9 moles) of 1-octadecanol (trade name: KALCOL 8098, the product of Kao Corporation), and as a solid acid catalyst, 700 g (10 wt % relative to the raw material alcohol) of γ-alumina (STREM Chemicals, Inc.) were placed, and reactions were allowed to proceed for 10 hours at 280° C. while stirring and passing nitrogen (7000 mL/minute) through the system. The alcohol conversion ratio was 100% and the purity of C18 internal olefin was 98.2% after the completion of the reaction. The resulting crude internal olefin was transferred to a distillation flask and distilled at the temperature inside of from 148 to 158° C./0.5 mmHg, whereby 100% pure purified internal olefin having 18 carbon atoms was obtained. The double bond distribution in the resulting internal olefin was 0.8% by mass at C-1 position, 31.3% by mass at C-2 position, 22.9% by mass at C-3 position, 15.5% by mass at C-4 position, 10.8% by mass at C-5 position, 7.2% by mass at C-6 position, 5.3% by mass at C-7 position, and 6.2% by mass in total at C-8 and 9 positions.

Production Example E

A reaction time was adjusted in the same manner as Production Example C, in order to produce C16 internal olefin having 100% of purity. The double bond distribution of the resulting internal olefin was 0.8% by mass at a C-1 position, 26.8% by mass at a C-2 position, 22.6% by mass at a C-3 position, 18.2% by mass at a C-4 position, 16.5% by mass at a C-5 position, 8.5% by mass at a C-6 position, and 6.6% by mass in total at C-7 and C-8 positions.

Production Example F

A reaction time was adjusted in a same manner as Production Example D, in order to produce C18 internal olefin having 100% of purity. The double bond distribution of the resulting internal olefin was 0.3% by mass at a C-1 position, 19.0% by mass at a C-2 position, 17.6% by mass at a C-3 position, 17.4% by mass at a C-4 position, 14.9% by mass at a C-5 position, 12.3% by mass at a C-6 position, 8.8% by mass at a C-7 position, and 9.8% by mass in total at C-8 and C-9 positions.

Production Example G 11.9 kg of the C16 internal olefin obtained in the Production Example E and 3.1 kg of the C18 internal olefin obtained in Production Example F were mixed to produce 15.0 kg of C16/C18 (mass ratio 79.4/20.6) internal olefin. The double bond distribution of the resulting internal olefin was 0.7% by mass at a C-1 position, 25.2% by mass at a C-2 position, 21.6% by mass at a C-3 position, 18.0% by mass at a C-4 position, 16.2% by mass at a C-5 position, 9.3% by mass at a C-6 position, 4.4% by mass at a C-7 position, 3.6% by mass at a C-8 position, and 1.0% by mass at a C-9 position.

Production Example H

A reaction time was adjusted in a same manner as Production Example C, in order to produce C16 internal olefin having 100% of purity. The double bond distribution of the resulting internal olefin was 0.5% by mass at a C-1 position, 30.1% by mass at a C-2 position, 25.5% by mass at a C-3 position, 18.9% by mass at a C-4 position, 11.1% by mass at a C-5 position, 7.0% by mass at a C-6 position, and 7.0% by mass in total at C-7 and C-8 positions.

Production Example I

A reaction time was adjusted in a same manner as Production Example D, in order to produce C18 internal olefin having 100% of purity. The double bond distribution of the resulting internal olefin was 0.5% by mass at a C-1 position, 25.0% by mass at a C-2 position, 22.8% by mass at a C-3 position, 19.1% by mass at a C-4 position, 14.0% by mass at a C-5 position, 7.4% by mass at a C-6 position, 5.4% by mass at a C-7 position, and 5.8% by mass in total at C-8 and C-9 positions.

Production Example J

Into a flask with a stirrer, 6000 g (30.6 moles) of 1-tetradecene (trade name: LINEALENE 14, the product of Idemitsu Kosan Co., Ltd.), and as a solid acid catalyst, 173 g (2.9 wt % relative to the raw material 1-tetradecene) of β-zeolite (Zeolyst International, Inc.) were placed, and reactions were allowed to proceed for 21 hours at 120° C. while stirring and passing nitrogen (200 mL/minute) through the system. The internal isomerization ratio of α-olefin was 99.0%, and the purity of C14 internal olefin was 91.1% after the completion of the reaction. The resulting crude internal olefin was transferred to a distillation flask and distilled at from 130 to 136° C./from 12.8 to 13.5 mmHg, whereby 100% pure internal olefin having 14 carbon atoms was obtained. The double bond distribution of the resulting internal olefin was 1.3% by mass at C-1 position, 31.8% by mass at C-2 position, 23.8% by mass at C-3 position, 21.0% by mass at C-4 position, 8.6% by mass at C-5 position, and 13.6% by mass in total at C-6 and C-7 positions.

Production Example K

Into a flask with a stirrer, 6000 g (35.6 moles) of 1-dodecene (trade name: LINEALENE 12, the product of Idemitsu Kosan Co., Ltd.), and as a solid acid catalyst, 180 g (3.0 wt % relative to the raw material 1-dodecene) of β-zeolite (Zeolyst International, Inc.) were placed, and reactions were allowed to proceed for 12.5 hours at 120° C. while stirring and passing nitrogen (200 mL/minute) through the system. The internal isomerization ratio of α-olefin was 98.4%, and the purity of C12 internal olefin was 92.1% after the completion of the reaction. The resulting crude internal olefin was transferred to a distillation flask and distilled at from 134 to 138° C./from 75.0 to 78.8 mmHg, whereby 100% pure internal olefin having 12 carbon atoms was obtained. The double bond distribution of the resulting internal olefin was 0.5% by mass at C-1 position, 33.1% by mass at C-2 position, 23.7% by mass at C-3 position, 21.2% by mass at C-4 position, 15.0% by mass at C-5 position, and 6.8% by mass at C-6 position.

(3) Production of an Internal Olefin Sulfonate

Production Example 1

Using a thin film sulfonation reactor (14 mm in inner diameter and 4 m in length), the sulfonation reaction of the internal olefin having 16 carbon atoms produced in Production Example C was carried out by passing through sulfur trioxide gas containing a concentration of $SO_3$ at 2.8% by volume, while passing cooling water of 20° C. through the outer jacket of the reactor. It should be noted that the reaction molar ratio of $SO_3$/internal olefin was set at 1.09.

The resulting sulfonation product was added to an alkaline aqueous solution containing 1.2 times the molar amount of sodium hydroxide relative to the theoretical acid value (AV), followed by neutralization at 30° C. for one hour while stirring. The resulting neutralized product was hydrolyzed by heating at 160° C. for one hour in an autoclave, whereby a crude product of sodium C16 internal olefin sulfonate was obtained.

Then, 300 g of the crude product thus obtained was transferred to a separatory funnel, to which 300 mL of ethanol was added. Then, 300 mL of petroleum ether was added per operation, whereby oil-soluble impurities were removed by extraction. At this time, inorganic compounds (mainly composed of sodium sulfate) which were precipitated at the oil-water interface by the addition of ethanol were also separated and removed from the aqueous phase by the oil-water separation operation. The above operation was repeated three times. Then, the aqueous phase side was evaporated to dryness, whereby sodium internal olefin sulfonate (1) having 16 carbon atoms was obtained. The content of the raw material internal olefin was less than 100 ppm (below the GC detection limit) and that of inorganic compounds was 1.9% by mass. The above results are shown in Table 1.

Production Example 2

Except for using the internal olefin having 18 carbon atoms produced in Production Example D, sodium internal olefin sulfonate (2) having 18 carbon atoms was obtained under the same conditions as those used in Production Example 1. The content of the raw material internal olefin was less than 100 ppm (below the GC detection limit) and that of inorganic compounds was 0.9% by mass. The above results are shown in Table 1.

Production Example 3

Except for using the internal olefin having 16 carbon atoms produced in Production Example B, sodium internal olefin sulfonate (3) having 16 carbon atoms was obtained under the same conditions as those used in Production Example 1. The content of the raw material internal olefin was less than 100 ppm (below the GC detection limit) and that of inorganic compounds was 1.3% by mass. The above results are shown in Table 1.

Production Example 4

Except for using the internal olefin having 18 carbon atoms produced in Production Example A, sodium internal olefin sulfonate (4) having 18 carbon atoms was obtained under the same conditions as those used in Production Example 1. The content of the raw material internal olefin was less than 100 ppm (below the GC detection limit) and that of inorganic compounds was 1.7% by mass. The above results are shown in Table 1.

Production Example 5

The C16/18 internal olefins (the content of internal olefin in which double bonds are present at C-2 position is 25.2% by mass) obtained in Production Example G was used as a raw material, and a sodium C16/C18 internal olefin sulfonate (5) was obtained by the same manner as in Production Example 1. The mass ratio of hydroxy form (sodium hydroxyalkane sulfonate)/olefin form (sodium olefin sulfonate) in the obtained sodium C16/18 internal olefin sulfonate was 87/13. Also, the content of the raw material internal olefin contained in the obtained sodium internal olefin sulfonate was less than 100 ppm (below the GC detection limit) and that of inorganic compounds was 0.5% by mass.

Production Example 6

Except for using the internal olefin having 16 carbon atoms produced in Production Example H, sodium internal olefin sulfonate (6) having 16 carbon atoms was obtained under the same conditions as those used in Production Example 1. The content of the raw material internal olefin was less than 100 ppm (below the GC detection limit) and that of inorganic compounds was 0.2% by mass. The above results are shown in Table 1.

Production Example 7

Except for using the internal olefin having 18 carbon atoms produced in Production Example I, sodium internal olefin sulfonate (7) having 18 carbon atoms was obtained under the same conditions as those used in Production Example 1. The content of the raw material internal olefin was less than 100 ppm (below the GC detection limit) and that of inorganic compounds was 0.1% by mass. The above results are shown in Table 1.

Production Example 8

Except for using the internal olefin having 14 carbon atoms produced in Production Example J, sodium internal olefin sulfonate (8) having 14 carbon atoms was obtained under the same conditions as those used in Production Example 1. The content of the raw material internal olefin was less than 100 ppm (below the GC detection limit) and that of inorganic compounds was 0.5% by mass. The above results are shown in Table 1.

Production Example 9

Except for using the internal olefin having 12 carbon atoms produced in Production Example K, sodium internal olefin sulfonate (9) having 12 carbon atoms was obtained under the same conditions as those used in Production Example 1. The content of the raw material internal olefin was less than 100 ppm (below the GC detection limit) and that of inorganic compounds was 0.2% by mass. The above results are shown in Table 1.

TABLE 1

| | Raw material internal olefin | | Internal olefin sulfonate | |
|---|---|---|---|---|
| | Number of carbon atoms | C-2 Double bond (%) | HAS/IOS(Mass ratio) | Content of internal olefin sulfonate in which sulfonate group is present at C-2 position (%) |
| Internal olefin sulfonate (1) | C16 | 30.4 | 80/20 | 20.3 |
| Internal olefin sulfonate (2) | C18 | 31.3 | 80/20 | 21.4 |
| Internal olefin sulfonate (3) | C16 | 16.5 | 80/20 | 9.3 |
| Internal olefin sulfonate (4) | C18 | 16.9 | 80/20 | 9.6 |
| Internal olefin sulfonate (5) | C16/C18 | 25.2 | 87/13 | 17.6 |
| Internal olefin sulfonate (6) | C16 | 30.1 | 80/20 | 19.9 |
| Internal olefin sulfonate (7) | C18 | 25.0 | 80/20 | 15.0 |
| Internal olefin sulfonate (8) | C14 | 31.8 | 92.8/7.4 | 22.0 |
| Internal olefin sulfonate (9) | C12 | 33.1 | 80/20 | 21.0 |

(4) Preparation of the Cleansing Compositions

Using internal olefin sulfonates shown in Table 1, the cleansing compositions for hair or skin each having the compositions shown in from Tables 2 to 7 were prepared by a conventional method. Specifically, the component (A) and appropriate amounts of water, and the components (B) to (M) if necessary, were taken in a beaker. The resulting mixture were heated to 60° C. and mixed, and then cooled to room temperature. Then, the mixture was supplemented with water and adjusted to pH 6 with a pH adjuster (a 50% aqueous solution of citric acid or a 10% aqueous solution of sodium hydroxide), whereby each cleansing composition was obtained.

TABLE 2

| | | | Formula Examples | | | | | | | | | |
|---|---|---|---|---|---|---|---|---|---|---|---|---|
| Cleansing composition | | | 1 | 2 | 3 | 4 | 5 | 6 | 7 | 8 | 9 | 10 |
| Blended composition (parts by mass) | (A) | Internal olefin sulfonate (1) | 4.8 | 8.0 | 8.0 | 8.0 | 8.0 | 8.0 | 8.0 | 8.0 | 8.0 | 8.0 |
| | | Internal olefin sulfonate (2) | 1.2 | 2.0 | 2.0 | 2.0 | 2.0 | 2.0 | 2.0 | 2.0 | 2.0 | 2.0 |
| | | Internal olefin sulfonate (5) | | | | | | | | | | |
| | (B) | Sodium laurylethersulfate*1 | 6.0 | | | | | | | | | |
| | | Sodium lauryl sulfate*2 | | | | | | | | | | |
| | (C) | Pseudo ceramide*3 | | 0.3 | | | | | | | | |
| | | Plant extracts*4 | | | | | | | | | | |
| | (D) | Triclosan*5 | | | 0.2 | | | | | | | |
| | | Benzalkonium chloride*6 | | | | | | | | | | |
| | (E) | Ethylene glycol distearate*7 | | | | 1.0 | | | | | | |
| | | Mixture of ethylene glycol distearate*8 | | | | | | | | | | |
| | (F) | Limonene*9 | | | | | 0.3 | | | | | |
| | | Menthol*10 | | | | | | | | | | |
| | (G) | Polypropylene glycol*11 | | | | | | 1.0 | | | | |
| | | Benzyl alcohol*12 | | | | | | | | | | |
| | (H) | Riboflavin*13 | | | | | | | | | | |
| | | D-panthenol*14 | | | | | | | 0.1 | | | |
| | (I) | Carboxyvinyl polymer*15 | | | | | | | | | | |
| | | Hydroxyethyl cellulose*16 | | | | | | | | 1.0 | | |
| | (J) | Sodium chloride | | | | | | | | | | |
| | | Sodium sulfate | | | | | | | | | 0.3 | |
| | (K) | EDTA | | | | | | | | | | |
| | | HEDP | | | | | | | | | | 0.5 |
| | | pH adjuster | q.s. | | | | | | | | | |
| | | Water | Balance | | | | | | | | | |

| | | | Formula Examples | | | | | | | | | |
|---|---|---|---|---|---|---|---|---|---|---|---|---|
| Cleansing composition | | | 11 | 12 | 13 | 14 | 15 | 16 | 17 | 18 | 19 | 20 |
| Blended composition (parts by mass) | (A) | Internal olefin sulfonate (1) | | | | | | | | | | |
| | | Internal olefin sulfonate (2) | | | | | | | | | | |
| | | Internal olefin sulfonate (5) | 6.0 | 10.0 | 10.0 | 10.0 | 10.0 | 10.0 | 10.0 | 10.0 | 10.0 | 10.0 |
| | (B) | Sodium laurylethersulfate*1 | 6.0 | | | | | | | | | |
| | | Sodium lauryl sulfate*2 | | | | | | | | | | |
| | (C) | Pseudo ceramide*3 | | 0.3 | | | | | | | | |
| | | Plant extracts*4 | | | | | | | | | | |
| | (D) | Triclosan*5 | | | 0.2 | | | | | | | |
| | | Benzalkonium chloride*6 | | | | | | | | | | |
| | (E) | Ethylene glycol distearate*7 | | | | 1.0 | | | | | | |
| | | Mixture of ethylene glycol distearate*8 | | | | | | | | | | |
| | (F) | Limonene*9 | | | | | 0.3 | | | | | |
| | | Menthol*10 | | | | | | | | | | |
| | (G) | Polypropylene glycol*11 | | | | | | 1.0 | | | | |
| | | Benzyl alcohol*12 | | | | | | | | | | |
| | (H) | Riboflavin*13 | | | | | | | | | | |
| | | D-panthenol*14 | | | | | | | 0.1 | | | |
| | (I) | Carboxyvinyl polymer*15 | | | | | | | | | | |
| | | Hydroxyethyl cellulose*16 | | | | | | | | 1.0 | | |
| | (J) | Sodium chloride | | | | | | | | | | |
| | | Sodium sulfate | | | | | | | | | 0.3 | |
| | (K) | EDTA | | | | | | | | | | |
| | | HEDP | | | | | | | | | | 0.5 |
| | | pH adjuster | q.s. | | | | | | | | | |
| | | Water | Balance | | | | | | | | | |

TABLE 3

| Cleansing composition | | | 21 | 22 | 23 | 24 | 25 | 26 | 27 | 28 | 29 | 30 | 31 | 32 | 33 | 34 | 35 | 36 | 37 | 38 | 39 | 40 |
|---|---|---|---|---|---|---|---|---|---|---|---|---|---|---|---|---|---|---|---|---|---|---|
| | | | Formula Examples | | | | | | | | | | | | | | | | | | | |
| Blended composition (parts by mass) | (A) | Internal olefin sulfonate (3) | 4.8 | 4.8 | 8.0 | 8.0 | 8.0 | 8.0 | 8.0 | 8.0 | 8.0 | 8.0 | 8.0 | 8.0 | 8.0 | 8.0 | 8.0 | 8.0 | 8.0 | 8.0 | 8.0 | 8.0 |
| | | Internal olefin sulfonate (4) | 1.2 | 1.2 | 2.0 | 2.0 | 2.0 | 2.0 | 2.0 | 2.0 | 2.0 | 2.0 | 2.0 | 2.0 | 2.0 | 2.0 | 2.0 | 2.0 | 2.0 | 2.0 | 2.0 | 2.0 |
| | (B) | Sodium lauryl-ethersulfate*[1] | 6.0 | | | | | | | | | | | | | | | | | | | |
| | | Sodium lauryl sulfate*[2] | | 6.0 | | | | | | | | | | | | | | | | | | |
| | (C) | Pseudo ceramide*[3] | | | 0.3 | | | | | | | | | | | | | | | | | |
| | | Plant extracts*[4] | | | | 0.1 | | | | | | | | | | | | | | | | |
| | (D) | Triclosan*[5] | | | | | 0.2 | | | | | | | | | | | | | | | |
| | | Benzalkonium chloride*[6] | | | | | | 0.5 | | | | | | | | | | | | | | |
| | (E) | Ethylene glycol distearate*[7] | | | | | | | 1.0 | | | | | | | | | | | | | |
| | | Mixture of ethylene glycol distearate*[8] | | | | | | | | 1.5 | | | | | | | | | | | | |
| | (F) | Limonene*[9] | | | | | | | | | 0.3 | | | | | | | | | | | |
| | | Menthol*[10] | | | | | | | | | | 0.5 | | | | | | | | | | |
| | (G) | Polypropylene glycol*[11] | | | | | | | | | | | 1.0 | | | | | | | | | |
| | | Benzyl alcohol*[12] | | | | | | | | | | | | 0.3 | | | | | | | | |
| | (H) | Riboflavin*[13] | | | | | | | | | | | | | 0.1 | | | | | | | |
| | | D-panthenol*[14] | | | | | | | | | | | | | | 0.1 | | | | | | |
| | (I) | Carboxyvinyl polymer*[15] | | | | | | | | | | | | | | | 0.8 | | | | | |
| | | Hydroxyethyl cellulose*[16] | | | | | | | | | | | | | | | | 1.0 | | | | |
| | (J) | Sodium chloride | | | | | | | | | | | | | | | | | 0.5 | | | |
| | | Sodium sulfate | | | | | | | | | | | | | | | | | | 2.0 | | |
| | (K) | EDTA | | | | | | | | | | | | | | | | | | | 0.5 | |
| | | HEDP | | | | | | | | | | | | | | | | | | | | 0.5 |
| | | pH adjuster | | | | | | | | | | q.s. | | | | | | | | | | |
| | | Water | | | | | | | | | | Balance | | | | | | | | | | |

TABLE 4

| Cleansing composition | | | 41 | 42 | 43 | 44 | 45 | 46 | 47 | 48 | 49 | 50 |
|---|---|---|---|---|---|---|---|---|---|---|---|---|
| | | | Formula Examples | | | | | | | | | |
| Blended composition (parts by mass) | (A) | Internal olefin sulfonate (3) | | | | | | | | | | |
| | | Internal olefin sulfonate (4) | | | | | | | | | | |
| | | Internal olefin sulfonate (5) | 6.0 | 6.0 | 10.0 | 10.0 | 10.0 | 10.0 | 10.0 | 10.0 | 10.0 | 10.0 |
| | (B) | Sodium laurylethersulfate*[1] | 6.0 | | | | | | | | | |
| | | Sodium lauryl sulfate*[2] | | 6.0 | | | | | | | | |
| | (C) | Pseudo ceramide*[3] | | | 0.3 | | | | | | | |
| | | Plant extracts*[4] | | | | 0.1 | | | | | | |
| | (D) | Triclosan*[5] | | | | | 0.2 | | | | | |
| | | Benzalkonium chloride*[6] | | | | | | 0.5 | | | | |
| | (E) | Ethylene glycol distearate*[7] | | | | | | | 1.0 | | | |
| | | Mixture of ethylene glycol distearate*[8] | | | | | | | | 1.5 | | |
| | (F) | Limonene*[9] | | | | | | | | | 0.3 | |
| | | Menthol*[10] | | | | | | | | | | 0.5 |
| | (G) | Polypropylene glycol*[11] | | | | | | | | | | |
| | | Benzyl alcohol*[12] | | | | | | | | | | |
| | (H) | Riboflavin*[13] | | | | | | | | | | |
| | | D-panthenol*[14] | | | | | | | | | | |
| | (I) | Carboxyvinyl polymer*[15] | | | | | | | | | | |
| | | Hydroxyethyl cellulose*[16] | | | | | | | | | | |
| | (J) | Sodium chloride | | | | | | | | | | |
| | | Sodium sulfate | | | | | | | | | | |
| | (K) | EDTA | | | | | | | | | | |
| | | HEDP | | | | | | | | | | |
| | | pH adjuster | | | | | q.s. | | | | | |
| | | Water | | | | | Balance | | | | | |

| Cleansing composition | | | 51 | 52 | 53 | 54 | 55 | 56 | 57 | 58 | 59 | 60 |
|---|---|---|---|---|---|---|---|---|---|---|---|---|
| | | | Formula Examples | | | | | | | | | |
| Blended composition (parts by mass) | (A) | Internal olefin sulfonate (3) | | | | | | | | | | |
| | | Internal olefin sulfonate (4) | | | | | | | | | | |
| | | Internal olefin sulfonate (5) | 10.0 | 10.0 | 10.0 | 10.0 | 10.0 | 10.0 | 10.0 | 10.0 | 10.0 | 10.0 |
| | (B) | Sodium laurylethersulfate*[1] | | | | | | | | | | |
| | | Sodium lauryl sulfate*[2] | | | | | | | | | | |
| | (C) | Pseudo ceramide*[3] | | | | | | | | | | |
| | | Plant extracts*[4] | | | | | | | | | | |

TABLE 4-continued

| | | | | | | | | | | | | |
|---|---|---|---|---|---|---|---|---|---|---|---|---|
| | (D) | Triclosan*[5] | | | | | | | | | | |
| | | Benzalkonium chloride*[6] | | | | | | | | | | |
| | (E) | Ethylene glycol distearate*[7] | | | | | | | | | | |
| | | Mixture of ethylene glycol distearate*[8] | | | | | | | | | | |
| | (F) | Limonene*[9] | | | | | | | | | | |
| | | Menthol*[10] | | | | | | | | | | |
| | (G) | Polypropylene glycol*[11] | 1.0 | | | | | | | | | |
| | | Benzyl alcohol*[12] | | 0.3 | | | | | | | | |
| | (H) | Riboflavin*[13] | | | 0.1 | | | | | | | |
| | | D-panthenol*[14] | | | | 0.1 | | | | | | |
| | (I) | Carboxyvinyl polymer*[15] | | | | | 0.8 | | | | | |
| | | Hydroxyethyl cellulose*[16] | | | | | | 1.0 | | | | |
| | (J) | Sodium chloride | | | | | | | 0.5 | | | |
| | | Sodium sulfate | | | | | | | | 2.0 | | |
| | (K) | EDTA | | | | | | | | | 0.5 | |
| | | HEDP | | | | | | | | | | 0.5 |
| | | pH adjuster | q.s. | | | | | | | | | |
| | | Water | Balance | | | | | | | | | |

TABLE 5

| | | | Formula Examples | | | | | | | | | | | | | |
|---|---|---|---|---|---|---|---|---|---|---|---|---|---|---|---|---|
| Cleansing composition | | | 61 | 62 | 63 | 64 | 65 | 66 | 67 | 68 | 69 | 70 | 71 | 72 | 73 | 74 |
| Blended composition (parts by mass) | (A) | Internal olefin sulfonate (6) | 4.8 | 4.8 | 8.0 | 8.0 | 8.0 | 8.0 | 8.0 | 8.0 | 8.0 | 8.0 | 8.0 | 8.0 | 8.0 | 8.0 |
| | | Internal olefin sulfonate (7) | 1.2 | 1.2 | 2.0 | 2.0 | 2.0 | 2.0 | 2.0 | 2.0 | 2.0 | 2.0 | 2.0 | 2.0 | 2.0 | 2.0 |
| | | Internal olefin sulfonate (8) | | | | | | | | | | | | | | |
| | | Internal olefin sulfonate (9) | | | | | | | | | | | | | | |
| | (B) | Sodium laurylethersulfonate*[1] | 6.0 | | | | | | | | | | | | | |
| | | Sodium lauryl sulfate*[2] | | 6.0 | | | | | | | | | | | | |
| | (C) | Pseudo ceramide*[3] | | | 0.3 | | | | | | | | | | | |
| | | Plant extracts*[4] | | | | 0.1 | | | | | | | | | | |
| | (D) | Triclosan*[5] | | | | | 0.2 | | | | | | | | | |
| | | Benzalkonium chloride*[6] | | | | | | 0.5 | | | | | | | | |
| | (E) | Ethylene glycol distearate*[7] | | | | | | | 1.0 | | | | | | | |
| | | Mixture of ethlene glycol distearate*[8] | | | | | | | | 1.5 | | | | | | |
| | (F) | Limonene*[9] | | | | | | | | | 0.3 | | | | | |
| | | Menthol*[10] | | | | | | | | | | 0.5 | | | | |
| | (G) | Polypropylene glycol*[11] | | | | | | | | | | | 1.0 | | | |
| | | Benzyl alcohol*[12] | | | | | | | | | | | | 0.3 | | |
| | (H) | Riboflavin*[13] | | | | | | | | | | | | | 0.1 | |
| | | D-panthenol*[14] | | | | | | | | | | | | | | 0.1 |
| | (I) | Carboxyvinyl polymer*[15] | | | | | | | | | | | | | | |
| | | Hydroxyethyl cellulose*[16] | | | | | | | | | | | | | | |
| | (J) | Sodium chloride | | | | | | | | | | | | | | |
| | | Sodium sulfate | | | | | | | | | | | | | | |
| | (K) | EDTA | | | | | | | | | | | | | | |
| | | HEDP | | | | | | | | | | | | | | |
| | | pH adjuster | q.s. | | | | | | | | | | | | | |
| | | Water | Balance | | | | | | | | | | | | | |

| | | | Formula Examples | | | | | | | | | | | | | |
|---|---|---|---|---|---|---|---|---|---|---|---|---|---|---|---|---|
| Cleansing composition | | | 75 | 76 | 77 | 78 | 79 | 80 | 81 | 82 | 83 | 84 | 85 | 86 | 87 | 88 |
| Blended composition (parts by mass) | (A) | Internal olefin sulfonate (6) | 8.0 | 8.0 | 8.0 | 8.0 | 8.0 | 8.0 | | | | | 2.4 | 2.4 | 2.4 | 2.4 |
| | | Internal olefin sulfonate (7) | 2.0 | 2.0 | 2.0 | 2.0 | 2.0 | 2.0 | | | | | 0.6 | 0.6 | 0.6 | 0.6 |
| | | Internal olefin sulfonate (8) | | | | | | | 6.0 | | 6.0 | | 3.0 | 3.0 | | |
| | | Internal olefin sulfonate (9) | | | | | | | | 6.0 | | 6.0 | | | 3.0 | 3.0 |
| | (B) | Sodium laurylethersulfonate*[1] | | | | | | | 6.0 | 6.0 | | | 6.0 | | 6.0 | |
| | | Sodium lauryl sulfate*[2] | | | | | | | | | 6.0 | 6.0 | | 6.0 | | 6.0 |
| | (C) | Pseudo ceramide*[3] | | | | | | | | | | | | | | |
| | | Plant extracts*[4] | | | | | | | | | | | | | | |
| | (D) | Triclosan*[5] | | | | | | | | | | | | | | |
| | | Benzalkonium chloride*[6] | | | | | | | | | | | | | | |
| | (E) | Ethylene glycol distearate*[7] | | | | | | | | | | | | | | |
| | | Mixture of ethlene glycol distearate*[8] | | | | | | | | | | | | | | |
| | (F) | Limonene*[9] | | | | | | | | | | | | | | |
| | | Menthol*[10] | | | | | | | | | | | | | | |
| | (G) | Polypropylene glycol*[11] | | | | | | | | | | | | | | |
| | | Benzyl alcohol*[12] | | | | | | | | | | | | | | |
| | (H) | Riboflavin*[13] | | | | | | | | | | | | | | |
| | | D-panthenol*[14] | | | | | | | | | | | | | | |
| | (I) | Carboxyvinyl polymer*[15] | 0.8 | | | | | | | | | | | | | |
| | | Hydroxyethyl cellulose*[16] | | 1.0 | | | | | | | | | | | | |

TABLE 5-continued

| | | | | | | |
|---|---|---|---|---|---|---|
| (J) | Sodium chloride | 0.5 | | | | |
| | Sodium sulfate | | 2.0 | | | |
| (K) | EDTA | | | 0.5 | | |
| | HEDP | | | | 0.5 | |
| | pH adjuster | | | | | q.s. |
| | Water | | | | | Balance |

*1: made by Kao Corporation, trade name: EMAL 270J (effective component of 70%)

*2: made by Kao Corporation, trade name: EMAL 30NS

*3: made by Kao Corporation, trade name: SOFCARE Ceramide SL-E

*4: made by ICHIMARU PHARCOS Co., Ltd., trade name: aloe vera extract (effective component of 1%)

*5: made by Ciba-Geigy AG, trade name: Irgasan DP-300

*6: made by Kao Corporation, trade name: SANISOL C (effective component of 50%)

*7: made by Kao Corporation, trade name: EMANON 3201M-V

*8: made by Cognis GmbH, trade name: Euperlan PK-3000 (effective component of 20%)

*9: made by Yamakei Sangyo K.K.

*10: made by The Suzuki Menthol Co., Ltd., trade name: 1-menthol

*11: made by Sanyo Chemical Industries, Ltd., trade name: NEWPOL PP-1000

*12: made by TAKASAGO INTERNATIONAL CORPORATION

*13: made by DSM Nutritional Japan K.K.

*14: made by BASF SE, trade name: D-panthenol 50P (effective component of 50%)

*15: made by Lubrizol Advanced Materials, Inc., trade name: Carbopol 980

*16: made by DAICEL CHEMICAL INDUSTRIES, LTD., trade name: HEC DAICEL HE850

TABLE 6

| | Cleansing compositionsing | Formula Examples | | | | | | | | | |
|---|---|---|---|---|---|---|---|---|---|---|---|
| | (Blended composition (parts by mass)) | 89 | 90 | 91 | 92 | 93 | 94 | 95 | 96 | 97 | 98 |
| (A) | Internal olefin sulfonate (1) | 8.0 | 8.0 | 8.0 | 8.0 | 9.0 | 7.0 | 8.0 | 8.0 | 4.0 | 12.0 |
| | Internal olefin sulfonate (2) | 2.0 | 2.0 | 2.0 | 2.0 | 1.0 | 3.0 | 2.0 | 2.0 | 1.0 | 3.0 |
| (B) | Sodium laurylphosphate*17 | | | | 3.0 | | | 6.0 | | | |
| | Sodium cocoyl glutamate*18 | | | 5.0 | | | | | | | |
| | Sodium cocoyl methyltaurine*19 | | | | | 2.0 | | | 5.0 | | |
| | Sodium laurylethersulfate*20 | | | | 2.0 | | 5.0 | | 3.0 | 6.0 | |
| | Palm oil fatty acid amidepropylbetaine*21 | 1.5 | | | | 1.0 | | 1.0 | 1.0 | | |
| | Betaine lauryldimethylaminoacetate*22 | | 2.4 | | | | | | | | |
| | PPG-5CETETH-20*23 | 0.5 | 0.5 | | | | | | | | |
| | Palm oil fatty acid monoethanolamide*24 | | | 1.0 | 1.0 | | | | 1.0 | | 0.7 |
| | Cetyltrimethylammonium chloride*25 | | | | | 0.1 | | | | | |
| (C) | *Eucalyptus* extract*26 | 0.1 | | 0.1 | | | | | | | |
| | Chamomile flower extract*27 | | | | 0.02 | | | 0.05 | | | |
| | Sugarcane extract | 0.1 | 0.05 | | | | | | | | |
| | Tea leaf extract | 0.1 | | | | | | | | | |
| | Lemone peel extract | 0.1 | | | | | | | | | |
| | Avocado extract | | 0.15 | | | | | | | | |
| | Sodium hyaluronate*28 | | | | | 0.1 | | | 0.02 | | 0.1 |
| | Sodium pyrrolidonecarboxylate*29 | | | | | 0.4 | | | | | |
| | Pseudo ceramide*30 | | | 1.0 | | | | | | | |
| | Glycerol*31 | 1.2 | | | | | | | | | 4.0 |
| (D) | Triclocarban | | | | 0.2 | | | | 0.2 | | |
| | Piroctone olamine*32 | | | | | | 0.5 | | | | |
| | Zinc pyrithione | | | | | 0.5 | | | | | |
| | Benzalkonium cetyl phosphate*33 | | | | | | | 1.0 | | | |
| | Salicylic acid | 0.1 | 0.5 | | | | 0.1 | | 0.2 | | |
| | Benzalkonium chloride*34 | | | | 1.0 | | | | | | |
| (E) | Ethylene glycol distearate*35 | | | 1.0 | | | | | | | |
| | Ethylene glycol distearate*36 | | | | 1.0 | | | | | | |
| | Ethylene glycol distearate*37 | | | | | 0.7 | | | | | |
| | Ethylene glycol distearate*38 | | | | | | 1.4 | | | | |
| | Ethylene glycol distearate*39 | | | | | | | | | | 1.0 |
| | Ethylene glycol distearate*40 | | | | | | | | 1.0 | | |
| | Ethylene glycol distearate*41 | | | | | | | | | 1.0 | |
| | Mica | 0.2 | | | | | | | | 1.0 | |
| | Tin oxide | 0.2 | | | | | | | | 1.0 | |
| (F) | Linalool | | 0.2 | 0.05 | 0.03 | | 0.1 | | | 0.05 | |
| | Ambroxan | | | 0.05 | | | | | | | |
| | Eugenol | | | 0.05 | | | | | | | |
| | Pearlide | | | | 0.03 | | | | | | |
| | HELIOL | | | | 0.03 | | 0.05 | | | | |
| | Limonene*42 | 0.3 | 0.1 | 0.1 | | 0.3 | | 0.3 | | | 3.0 |
| | α-Isomethylionone | 0.1 | | | | | | | | | |
| | Hexylcinnamal | 0.1 | 0.1 | | | | | | | | |

TABLE 6-continued

| | Cleansing compositionsing | Formula Examples | | | | | | | | | |
|---|---|---|---|---|---|---|---|---|---|---|---|
| | (Blended composition (parts by mass)) | 89 | 90 | 91 | 92 | 93 | 94 | 95 | 96 | 97 | 98 |
| (G) | Benzyloxyethanol | | | 0.5 | 0.25 | | | | | | 0.1 |
| | Ethylene glycol dibutyl ether | | | | | 0.3 | | | | | |
| | Polyethylene glycol (average molecular weight of 400) | | | | | 0.3 | | | | | |
| | Polypropylene glycol*[43] | | | | 1.0 | | | | | | |
| (H) | Retinol | | | | | 0.05 | | | | | |
| | DI-tocopherol | | | | | 0.05 | | | | | |
| | Ascorbic acid | | | | | 0.05 | | | 0.1 | | |
| | D-panthenol*[44] | | | | 0.1 | | | | | | |
| | Pyridoxine HCl (vitamin B)*[45] | 0.1 | 0.2 | | | | | | | | |
| (I) | Hydroxypropyl cellulose*[46] | | | | | 0.3 | | | | | |
| | Guar gum*[47] | | | | | | 0.2 | | | | |
| | Sodium polyacrylate*[48] | | | | | | | | | 0.3 | |
| | Carboxyvinyl polymer*[49] | | 0.5 | | 0.3 | | | 0.2 | | | 0.5 |
| | Acrylic acid alkyl copolymer*[50] | 0.3 | | | | | | | | | |
| (J) | Sodium chloride | | | 0.5 | | | 1.1 | | | | |
| | Trisodium citrate | | | | 0.2 | | | 0.4 | | | |
| | Disodium succinate | | | | | 0.35 | | | 0.3 | 0.3 | |
| (K) | EDTA-3Na*[51] | | | 0.2 | | 0.05 | | 0.75 | | | |
| | Etidronic acid (diphosphonic acid)*[52] | | | | 0.1 | | | | 0.02 | | |
| (L) | Silicone*[53] | 1.0 | | | 2.8 | | 1.4 | | | | |
| | Amino-modified silicone*[54] | | 0.5 | | | 0.3 | | | | | |
| | Behenyl alcohol*[55] | 0.1 | | | | | | | | | |
| | Glyceryl eicosanoate*[56] | 0.05 | 0.2 | | | | | | | | |
| (M) | Cationated guar gum*[57] | 0.3 | | | 0.2 | | 0.4 | | | | |
| | Diallyl quaternary ammonium salt polymer*[58] | | 0.2 | | | | | | 0.90 | | |
| | Diallyl quaternary ammonium salt/acrylamide copolymer*59 | | | 0.2 | | | | | | | 0.1 |
| | pH adjuster | | | | | q.s. | | | | | |
| | Water | | | | | Balance | | | | | |

TABLE 7

| | Cleansing compositionsing | Formula Examples | | | | | |
|---|---|---|---|---|---|---|---|
| | (Blended composition (parts by mass)) | 99 | 100 | 101 | 102 | 103 | 104 |
| (A) | Internal olefin sulfonate (5) | 10.0 | 10.0 | 10.0 | 10.0 | 10.0 | 10.0 |
| (B) | Sodium laurylphosphate*[17] | | | | 3.0 | 6.0 | |
| | Sodium cocoyl glutamate*[18] | | | 5.0 | | | |
| | Sodium cocoyl methyltaurine*[19] | | | | | | 5.0 |
| | Sodium laurylethersulfate*[20] | | | | 2.0 | | 3.0 |
| | Palm oil fatty acid amidepropylbetaine*[21] | 1.5 | | | | 1.0 | 1.0 |
| | Betaine lauryldimethylaminoacetate*[22] | | 2.4 | | | | |
| | PPG-5CETETH-20*[23] | 0.5 | 0.5 | | | | |
| | Palm oil fatty acid monoethanolamide*[24] | | | 1.0 | 1.0 | | 1.0 |
| | Cetyltrimethylammonium chloride*[25] | | | | | | |
| (C) | *Eucalyptus* extract*[26] | 0.1 | | 0.1 | | | |
| | Chamomile flower extract*[27] | | | | 0.02 | 0.05 | |
| | Sugarcane extract | 0.1 | 0.05 | | | | |
| | Tea leaf extract | 0.1 | | | | | |
| | Lemone peel extract | 0.1 | | | | | |
| | Avocado extract | | 0.15 | | | | |
| | Sodium hyaluronate*[28] | | | | | | 0.02 |
| | Sodium pyrrolidonecarboxylate*[29] | | | | | | |
| | Pseudo ceramide*[30] | | | 1.0 | | | |
| | Glycerol*[31] | 1.2 | | | | | |
| (D) | Triclocarban | | | | 0.2 | | 0.2 |
| | Piroctone olamine*[32] | | | | | | |
| | Zinc pyrithione | | | | | | |
| | Benzalkonium cetyl phosphate*[33] | | | | | 1.0 | |
| | Salicylic acid | 0.1 | 0.5 | | | | 0.2 |
| | Benzalkonium chloride*[34] | | | | 1.0 | | |
| (E) | Ethylene glycol distearate*[35] | | | 1.0 | | | |
| | Ethylene glycol distearate*[36] | | | | 1.0 | | |
| | Ethylene glycol distearate*[37] | | | | | | |
| | Ethylene glycol distearate*[38] | | | | | | |
| | Ethylene glycol distearate*[39] | | | | | | |
| | Ethylene glycol distearate*[40] | | | | | | 1.0 |
| | Ethylene glycol distearate*[41] | | | | | | |
| | Mica | 0.2 | | | | | |
| | Tin oxide | 0.2 | | | | | |

TABLE 7-continued

| | Cleansing compositionsing (Blended composition (parts by mass)) | Formula Examples 99 | 100 | 101 | 102 | 103 | 104 |
|---|---|---|---|---|---|---|---|
| (F) | Linalool | | 0.2 | 0.05 | 0.03 | | |
| | Ambroxan | | | 0.05 | | | |
| | Eugenol | | | 0.05 | | | |
| | Pearlide | | | | 0.03 | | |
| | HELIOL | | | | 0.03 | | |
| | Limonene*[42] | 0.3 | 0.1 | 0.1 | | 0.3 | |
| | α-Isomethylionone | 0.1 | | | | | |
| | Hexylcinnamal | 0.1 | 0.1 | | | | |
| (G) | Benzyloxyethanol | | | 0.5 | 0.25 | | |
| | Ethylene glycol dibutyl ether | | | | | | |
| | Polyethylene glycol (average molecular weight of 400) | | | | | | |
| | Polypropylene glycol*[43] | | | | 1.0 | | |
| (H) | Retinol | | | | | | |
| | DI-tocopherol | | | | | | |
| | Ascorbic acid | | | | | | 0.1 |
| | D-panthenol*[44] | | | | 0.1 | | |
| | Pyridoxine HCl (vitamin B)*[45] | 0.1 | 0.2 | | | | |
| (I) | Hydroxypropyl cellulose*[46] | | | | | | |
| | Guar gum*[47] | | | | | | |
| | Sodium polyacrylate*[48] | | | | | | |
| | Carboxyvinyl polymer*[49] | | 0.5 | | 0.3 | 0.2 | |
| | Acrylic acid alkyl copolymer*[50] | 0.3 | | | | | |
| (J) | Sodium chloride | | | 0.5 | | | |
| | Trisodium citrate | | | | 0.2 | 0.4 | |
| | Disodium succinate | | | | | | 0.3 |
| (K) | EDTA-3Na *[51] | | | 0.2 | | 0.75 | |
| | Etidronic acid (diphosphonic acid)*[52] | | | | 0.1 | | 0.02 |
| (L) | Silicone*[53] | 1.0 | | | 2.8 | | |
| | Amino-modified silicone*[54] | | 0.5 | | | | |
| | Behenyl alcohol*[55] | 0.1 | | | | | |
| | Glyceryl eicosanoate*[56] | 0.05 | 0.2 | | | | |
| (M) | Cationated guar gum*[57] | 0.3 | | | 0.2 | | |
| | Diallyl quaternary ammonium salt polymer*[58] | | 0.2 | | | | 0.90 |
| | Diallyl quaternary ammonium salt/acrylamide copolymer*[59] | | | 0.2 | | | |
| | pH adjuster | | | q.s. | | | |
| | Water | | | Balance | | | |

TABLE 8

| | Cleansing composition (Blended composition (parts by mass)) | Formula Examples 105 | 106 | 107 | 108 | 109 | 110 | 111 | 112 | 113 | 114 |
|---|---|---|---|---|---|---|---|---|---|---|---|
| (A) | Internal olefin sulfonate (3) | 8.0 | 8.0 | 8.0 | 8.0 | 9.0 | 7.0 | 8.0 | 8.0 | 4.0 | 12.0 |
| | Internal olefin sulfonate (4) | 2.0 | 2.0 | 2.0 | 2.0 | 1.0 | 3.0 | 2.0 | 2.0 | 1.0 | 3.0 |
| (B) | Sodium laurylphosphate*[17] | | | | 3.0 | | | 6.0 | | | |
| | Sodium cocoyl glutamate*[18] | | | 5.0 | | | | | | | |
| | Sodium cocoyl methyltaurine*[19] | | | | | 2.0 | | | 5.0 | | |
| | Sodium laurylethersulfate*[20] | | | | 2.0 | | 5.0 | | 3.0 | 6.0 | |
| | Palm oil fatty acid amidepropylbetaine*[21] | 1.5 | | | | 1.0 | | 1.0 | 1.0 | | |
| | Betaine lauryldimethylaminoacetate*[22] | | 2.4 | | | | | | | | |
| | PPG-5CETETH-20*[23] | 0.5 | 0.5 | | | | | | | | |
| | Palm oil fatty acid monoethanolamide*[24] | | | 1.0 | 1.0 | | | | 1.0 | | 0.7 |
| | Cetyltrimethylammonium chloride*[25] | | | | | 0.1 | | | | | |
| (C) | *Eucalyptus* extract*[26] | 0.1 | | 0.1 | | | | | | | |
| | Chamomile flower extract*[27] | | | | 0.02 | | | 0.05 | | | |
| | Sugarcane extract | 0.1 | 0.05 | | | | | | | | |
| | Tea leaf extract | 0.1 | | | | | | | | | |
| | Lemone peel extract | 0.1 | | | | | | | | | |
| | Avocado extract | | 0.15 | | | | | | | | |
| | Sodium hyaluronate*[28] | | | | | 0.1 | | | 0.02 | | 0.1 |
| | Sodium pyrrolidonecarboxylate*[29] | | | | | 0.4 | | | | | |
| | Pseudo ceramide*[30] | | | 1.0 | | | | | | | |
| | Glycerol*[31] | 1.2 | | | | | | | | | 4.0 |
| (D) | Triclocarban | | | | 0.2 | | | | 0.2 | | |
| | Piroctone olamine*[32] | | | | | | 0.5 | | | | |
| | Zinc pyrithione | | | | | 0.5 | | | | | |
| | Benzalkonium cetyl phosphate*[33] | | | | | | | 1.0 | | | |
| | Salicylic acid | 0.1 | 0.5 | | | | 0.1 | | 0.2 | | |
| | Benzalkonium chloride*[34] | | | | 1.0 | | | | | | |
| (E) | Ethylene glycol distearate*[35] | | | 1.0 | | | | | | | |
| | Ethylene glycol distearate*[36] | | | | 1.0 | | | | | | |

TABLE 8-continued

| | Cleansing composition (Blended composition (parts by mass)) | Formula Examples 105 | 106 | 107 | 108 | 109 | 110 | 111 | 112 | 113 | 114 |
|---|---|---|---|---|---|---|---|---|---|---|---|
| | Ethylene glycol distearate*[37] | | | | | 0.7 | | | | | |
| | Ethylene glycol distearate*[38] | | | | | | 1.4 | | | | |
| | Ethylene glycol distearate*[39] | | | | | | | | | | 1.0 |
| | Ethylene glycol distearate*[40] | | | | | | | | 1.0 | | |
| | Ethylene glycol distearate*[41] | | | | | | | | | 1.0 | |
| | Mica | 0.2 | | | | | | | | 1.0 | |
| | Tin oxide | 0.2 | | | | | | | | 1.0 | |
| (F) | Linalool | | 0.2 | 0.05 | 0.03 | | 0.1 | | | 0.05 | |
| | Ambroxan | | | 0.05 | | | | | | | |
| | Eugenol | | | 0.05 | | | | | | | |
| | Pearlide | | | | 0.03 | | | | | | |
| | HELIOL | | | | 0.03 | | 0.05 | | | | |
| | Limonene*[42] | 0.3 | 0.1 | 0.1 | | 0.3 | | 0.3 | | | 3.0 |
| | α-Isomethylionone | 0.1 | | | | | | | | | |
| | Hexylcinnamal | 0.1 | 0.1 | | | | | | | | |
| (G) | Benzyloxyethanol | | | 0.5 | 0.25 | | | | | | 0.1 |
| | Ethylene glycol dibutyl ether | | | | | 0.3 | | | | | |
| | Polyethylene glycol (average molecular weight of 400) | | | | | 0.3 | | | | | |
| | Polypropylene glycol*[43] | | | | 1.0 | | | | | | |
| (H) | Retinol | | | | | 0.05 | | | | | |
| | DI-tocopherol | | | | | 0.05 | | | | | |
| | Ascorbic acid | | | | | 0.05 | | | 0.1 | | |
| | D-panthenol*[44] | | | | 0.1 | | | | | | |
| | Pyridoxine HCl (vitamin B)*[45] | 0.1 | 0.2 | | | | | | | | |
| (I) | Hydroxypropyl cellulose*[46] | | | | | 0.3 | | | | | |
| | Guar gum*[47] | | | | | | 0.2 | | | | |
| | Sodium polyacrylate*[48] | | | | | | | | | 0.3 | |
| | Carboxyvinyl polymer*[49] | | 0.5 | | 0.3 | | | 0.2 | | | 0.5 |
| | Acrylic acid alkyl copolymer*[50] | 0.3 | | | | | | | | | |
| (J) | Sodium chloride | | | 0.5 | | | 1.1 | | | | |
| | Trisodium citrate | | | | 0.2 | | | 0.4 | | | |
| | Disodium succinate | | | | | 0.35 | | | 0.3 | 0.3 | |
| (K) | EDTA-3Na *[51] | | | 0.2 | | 0.05 | | 0.75 | | | |
| | Etidronic acid (diphosphonic acid)*[52] | | | | 0.1 | | | | 0.02 | | |
| (L) | Silicone*[53] | 1.0 | | | 2.8 | | 1.4 | | | | |
| | Amino-modified silicone*[54] | | 0.5 | | | 0.3 | | | | | |
| | Behenyl alcohol*[55] | 0.1 | | | | | | | | | |
| | Glyceryl eicosanoate*[56] | 0.05 | 0.2 | | | | | | | | |
| (M) | Cationated guar gum*[57] | 0.3 | | | 0.2 | | 0.4 | | | | |
| | Diallyl quaternary ammonium salt polymer*[58] | | 0.2 | | | | | | 0.90 | | |
| | Diallyl quaternary ammonium salt/acrylamide copolymer*[59] | | | 0.2 | | | | | | | 0.1 |
| | pH adjuster | | | | | q.s. | | | | | |
| | Water | | | | | Balance | | | | | |

TABLE 9

| | Cleansing composition (Blended composition (parts by mass)) | Formula Examples 115 | 116 | 117 | 118 | 119 | 120 | 121 | 122 | 123 | 124 | 125 | 126 |
|---|---|---|---|---|---|---|---|---|---|---|---|---|---|
| (A) | Internal olefin sulfonate (6) | 8.0 | 8.0 | 8.0 | 8.0 | 8.0 | 8.0 | 4.0 | 4.0 | 4.0 | 4.0 | 4.0 | 4.0 |
| | Internal olefin sulfonate (7) | 2.0 | 2.0 | 2.0 | 2.0 | 2.0 | 2.0 | 1.0 | 1.0 | 1.0 | 1.0 | 1.0 | 1.0 |
| | Internal olefin sulfonate (8) | | | | | | | 5.0 | | 2.5 | 5.0 | | 2.5 |
| | Internal olefin sulfonate (9) | | | | | | | | 5.0 | 2.5 | | 5.0 | 2.5 |
| (B) | Sodium laurylphosphate*[17] | | | | 3.0 | 6.0 | | | | | 3.0 | 6.0 | |
| | Sodium cocoyl glutamate*[18] | | | 5.0 | | | | | | 5.0 | | | |
| | Sodium cocoyl methyltaurine*[19] | | | | | | 5.0 | | | | | | 5.0 |
| | Sodium laurylethersulfate*[20] | | | | 2.0 | | 3.0 | | | | 2.0 | | 3.0 |
| | Palm oil fatty acid amidepropylbetaine*[21] | 1.5 | | | | 1.0 | 1.0 | 1.5 | | | | 1.0 | 1.0 |
| | Betaine lauryldimethylaminoacetate*[22] | | 2.4 | | | | | | 2.4 | | | | |
| | PPG-5CETETH-20*[23] | 0.5 | 0.5 | | | | | 0.5 | 0.5 | | | | |
| | Palm oil fatty acid monoethanoiamide*[24] | | | 1.0 | 1.0 | | 1.0 | | | 1.0 | 1.0 | | 1.0 |
| | Cetyltrimethylammonium chloride*[25] | | | | | | | | | | | | |
| (C) | *Eucalyptus* extract*[26] | 0.1 | | 0.1 | | | | 0.1 | | 0.1 | | | |
| | Chamomile flower extract*[27] | | | | 0.02 | 0.05 | | | | | 0.02 | 0.05 | |
| | Sugarcane extract | 0.1 | 0.05 | | | | | 0.1 | 0.05 | | | | |
| | Tea leaf extract | 0.1 | | | | | | 0.1 | | | | | |
| | Lemone peel extract | 0.1 | | | | | | 0.1 | | | | | |
| | Avocado extract | | 0.15 | | | | | | 0.15 | | | | |

TABLE 9-continued

| | Cleansing composition | Formula Examples | | | | | | | | | | | |
|---|---|---|---|---|---|---|---|---|---|---|---|---|---|
| | (Blended composition (parts by mass)) | 115 | 116 | 117 | 118 | 119 | 120 | 121 | 122 | 123 | 124 | 125 | 126 |
| | Sodium hyaluronate | | | | | | 0.02 | | | | | | 0.02 |
| | Sodium pyrrolidonecarboxylate*29 | | | | | | | | | | | | |
| | Pseudo ceramide*30 | | | 1.0 | | | | | | 1.0 | | | |
| | Glycerol*31 | 1.2 | | | | | | 1.2 | | | | | |
| (D) | Triclocarban | | | | 0.2 | | 0.2 | | | | 0.2 | | 0.2 |
| | Piroctone olamine*32 | | | | | | | | | | | | |
| | Zinc pyrithione | | | | | | | | | | | | |
| | Benzalkonium cetyl phosphate*33 | | | | | 1.0 | | | | | | 1.0 | |
| | Salicylic acid | 0.1 | 0.5 | | | | 0.2 | 0.1 | 0.5 | | | | 0.2 |
| | Benzalkonium chloride*34 | | | | 1.0 | | | | | | 1.0 | | |
| (E) | Ethylene glycol distearate*35 | | | 1.0 | | | | | | 1.0 | | | |
| | Ethylene glycol distearate*36 | | | | 1.0 | | | | | | 1.0 | | |
| | Ethylene glycol distearate*37 | | | | | | | | | | | | |
| | Ethylene glycol distearate*38 | | | | | | | | | | | | |
| | Ethylene glycol distearate*39 | | | | | | | | | | | | |
| | Ethylene glycol distearate*40 | | | | | | 1.0 | | | | | | 1.0 |
| | Ethylene glycol distearate*41 | | | | | | | | | | | | |
| | Mica | 0.2 | | | | | | 0.2 | | | | | |
| | Tin oxide | 0.2 | | | | | | 0.2 | | | | | |
| (F) | Linalool | | 0.2 | 0.05 | 0.03 | | | | 0.2 | 0.05 | 0.03 | | |
| | Ambroxan | | | 0.05 | | | | | | 0.05 | | | |
| | Eugenol | | | 0.05 | | | | | | 0.05 | | | |
| | Pearlide | | | | 0.03 | | | | | | 0.03 | | |
| | HELIOL | | | | 0.03 | | | | | | 0.03 | | |
| | Limonene*42 | 0.3 | 0.1 | 0.1 | | 0.3 | | 0.3 | 0.1 | 0.1 | | 0.3 | |
| | α-Isomethylionone | 0.1 | | | | | | 0.1 | | | | | |
| | Hexylcinnamal | 0.1 | 0.1 | | | | | 0.1 | 0.1 | | | | |
| (G) | Benzyloxyethanol | | | 0.5 | 0.25 | | | | | 0.5 | 0.25 | | |
| | Ethylene glycol dibutyl ether | | | | | | | | | | | | |
| | Polyethylene glycol (average molecular weight of 400) | | | | | | | | | | | | |
| | Polyoropylene glycol*43 | | | | 1.0 | | | | | | 1.0 | | |
| (H) | Retinol | | | | | | | | | | | | |
| | DI-tocopherol | | | | | | | | | | | | |
| | Ascorbic acid | | | | | | 0.1 | | | | | | 1.0 |
| | D-panthenol*44 | | | | 0.1 | | | | | | 0.1 | | |
| | Pyridoxine HCl (vitamin B)*45 | 0.1 | 0.2 | | | | | 0.1 | 0.2 | | | | |
| (I) | Hydroxypropyl cellulose*46 | | | | | | | | | | | | |
| | Guar gum*47 | | | | | | | | | | | | |
| | Sodium polyacrylate*48 | | | | | | | | | | | | |
| | Carboxyvinyl polymer*49 | | 0.5 | | 0.3 | 0.2 | | | 0.5 | | 0.3 | 0.2 | |
| | Acrylic acid alkyl copolymer*50 | 0.3 | | | | | | 0.3 | | | | | |
| (J) | Sodium chloride | | | 0.5 | | | | | | 0.5 | | | |
| | Trisodium citrate | | | | 0.2 | 0.4 | | | | | 0.2 | 0.4 | |
| | Disodium succinate | | | | | | 0.3 | | | | | | 0.3 |
| (K) | EDTA-3Na*51 | | | 0.2 | | 0.75 | | | | 0.2 | | 0.75 | |
| | Etidronic acid (diphosphonic acid)*52 | | | | 0.1 | | 0.02 | | | | 0.1 | | 0.02 |
| (L) | Silicone*53 | 1.0 | | | 2.8 | | | 1.0 | | | 2.8 | | |
| | Amino-modified silicone*54 | | 0.5 | | | | | | 0.5 | | | | |
| | Behenyl alcohol*55 | 0.1 | | | | | | 0.1 | | | | | |
| | Glyceryl eicosanoate*56 | 0.05 | 0.2 | | | | | 0.05 | 0.2 | | | | |
| (M) | Cationated guar gum*57 | 0.3 | | | 0.2 | | | 0.3 | | | 0.2 | | |
| | Diallyl quaternary ammonium salt polymer*58 | | 0.2 | | | | 0.90 | | 0.2 | | | | 0.90 |
| | Diallyl quaternary ammonium salt/acrylamide | | | 0.2 | | | | | | 0.2 | | | |
| | pH adjuster | | | | | | q.s. | | | | | | |
| | Water | | | | | | Balance | | | | | | |

*17: made by Nikko Chemicals Co., Ltd., trade name: NIKKOL SLP-N

*18: made by Ajinomoto Co., Inc., trade name: Amisoft CS-22 (effective component of 25%)

*19: made by Nikko Chemicals Co., Ltd., trade name: NIKKOL CMT-30 (effective component of 30%)

*20: made by Kao Corporation, trade name: EMAL 270J (effective component of 70%)

*21: made by Kao Corporation, trade name: AMPHITOL 55AB (effective component of 30%)

*22: made by Kao Corporation, trade name: AMPHITOL 20BS (effective component of 30%)

*23: made by Croda International Plc, trade name: Procetyl AWS

*24: made by Kawaken Fine Chemicals Co., Ltd., trade name: Amisol CME

*25: made by Kao Corporation, trade name: Cortamine 60W (effective component of 30%)

*26: made by ICHIMARU PHARCOS Co., Ltd., trade name: Pharcolex *Eucalyptus* B

*27: made by ICHIMARU PHARCOS Co., Ltd., trade name: Pharcolex BX44

*28: made by BASF Japan Ltd., trade name: Hyaluronic Filling Spheres

*29: made by Ajinomoto Co., Inc., trade name: PRODEW 300 (effective component of 10.55%)

*30: made by Kao Corporation, trade name: SOFCARE Ceramide SL-E

*31: made by Kao Corporation, trade name: concentrated glycerol for cosmetics

*32: made by Clariant International Ltd., trade name: Octopirox

*33: made by Kao Corporation, trade name: SANISOL P (effective component of 50%)

*34: made by Kao Corporation, trade name: SANISOL C (effective component of 50%)

*35: made by Cognis GmbH, trade name: Euperlan PK1200 (effective component of 20%)

*36: made by Cognis GmbH, trade name: Euperlan PK771 (effective component of 23%)

*37: made by Cognis GmbH, trade name: Euperlan PK810 (effective component of 20%)

*38: made by Cognis GmbH, trade name: Euperlan PK900 (effective component of 25%)

*39: made by Kao Corporation, trade name: PEARL CONCENTRATE SA-M2 (effective component of 20%)

*40: made by Kao Corporation, trade name: PEARL CONCENTRATE FC-1 (effective component of 20%)

*41: made by Kao Corporation, trade name: EMANON 3201M-V

*42: made by Yamakei Sangyo K.K.

*43: made by Sanyo Chemical Industries, Ltd., trade name: NEWPOL PP-1000

*44: made by BASF SE, trade name: D-panthenol 50P (effective component of 50%)

*45: made by DSM Nutritional Japan K.K., trade name: pyridoxine hydrochloride

*46: made by NIPPON SODA CO., LTD., trade name: CELNY M

*47: made by Evonik Goldschmidt GmbH, trade name: TEGO Emulprot

*48: made by ISP Japan K.K., trade name: LUBRAJEL IIXD FREE

*49: made by Lubrizol Advanced Materials, Inc., trade name: Carbopol 980

*50: made by Evonik Rohm GmbH, trade name: EUDRAGIT L100

*51: made by Nagase ChemteX Corporation, trade name: Clewat 3Na

*52: made by Themphos International B.V., trade name: DEQUEST 2010CS (effective component of 60%)

*53: made by Dow Corning Toray Co., Ltd., trade name: BY22-050 (effective component of 50%)

*54: made by Dow Corning Toray Co., Ltd., trade name: BY22-079 (effective component of 14%)

*55: made by Kao Corporation, trade name: KALCOL 220-80

*56: made by The Nisshin OilliO Group, Ltd., trade name: Nomcort HK-G

*57: made by Rhodia S. A., trade name: Jaguar C-13S)

*58: made by The Lubrizol Corporation, trade name: MERQUART 550

*59: made by The Lubrizol Corporation, trade name: MERQUART 2001

(5) Hair Evaluation after Washing

Each of the following components was placed in a beaker and heated to 80° C., followed by mixing. After confirming homogeneous dissolution, the mixture was cooled to give a plain shampoo. A hair bundle (Japanese hair which was never subjected to treatment such as bleaching and hair coloring, approximately cm long, 15 g) was washed with the plain shampoo thus obtained, whereby a tress for evaluation was obtained.

(Composition of the Plain Shampoo)

| (Component) | (% by mass) |
|---|---|
| Sodium polyoxyethylene lauryl ether sulfate (42.0% as EMAL E-27C (the product of Kao Corporation, active content, 27% by mass)) | 11.3 |
| Coconut oil fatty acid N-methyl ethanolamide (AMINON C-11S (the product of Kao Corporation)) | 3.0 |
| Citric acid | 0.2 |
| Methylparaben | 0.3 |
| Purified water | Balance |
| Total | 100.0 |

The tress for evaluation thus obtained was washed with each cleansing composition for hair, and five expert panelists evaluated the rinse feel after shampooing, combability of the hair after rinsing, and manageability of the hair after drying, based on the following evaluation criteria and evaluation method.

Also, in order to evaluate a foam retention (durability) in the presence of an oily component such as stain of sebum, 0.05 ml of model sebum was applied to the hair, and was washed. Then, foam durability during washing was evaluated. The model sebum was prepared by uniformly mixing 4/1% by mass of triolein/lanolin at 40° C.

(Evaluation Criteria and Evaluation Method)

Rinse Feel

5: Rinse feel is very good
4: Rinse feel is good
3: Rinse feel is ordinary
2: Rinse feel is bad
1: Rinse feel is very bad Combability 5: Combability is very good
4: Combability is good
3: Combability is ordinary
2: Combability is bad
1: Combability is very bad Manageability 5: Manageability of hair is very good
4: Manageability of hair is good
3: Manageability of hair is ordinary
2: Manageability of hair is bad
1: Manageability of hair is totally impossible Foam Durability 5: Foam durability is very good (not feeling a decrease in the volume of foam during washing)
4: Foam durability is good (less decrease in the volume of foam)
3: Ordinary foam durability
2: Foam durability was poor (remarkable decrease in the volume of foam)
1: Foam was not maintained (defoaming was found during washing)

(6) Skin Evaluation after Washing

Five expert panelists washed their hands with each cleansing composition for skin, and evaluated the rinse feel after washing, and the moist feeling to the skin after towel drying after rinsing, and durability of foam based on the following evaluation criteria and evaluation method. It should be noted that the rinse feel was evaluated based on the same criteria as those used for hair. Also, durability of foam was evaluated based on the same criteria as those used for hair by applying model sebum to the hand.

Moist Feeling

5: Very moist

4: Moist

3: Ordinary

2: Not moist

1: Not moist at all and feels roughness

It should be noted that the following formulation was regarded as an evaluation corresponding to "3: Ordinary", with reference to each evaluation criteria to rinse feel, combability, manageability, durability of foam, and moist feeling.

| (Component) | (% by mass) |
|---|---|
| Sodium laurylether sulfate *1 | 12.0 |
| pH adjuster | q.s. (adjusted to pH 6.0) |
| Purified water | Balance |
| Total | 100.0 |

*1: made by Kao Corporation, 17.14% of EMAL 270S (effective component of 70%) was added Example 127 (Hair Shampoo)

A hair shampoo having the composition below was produced as follows. Purified water, methylparaben, and a surfactant were placed in a beaker, and heated to 80° C. while stirring these. It was checked that these were uniformly dissolved. Silicone was added to the mixture after the mixture was cooled to 60° C. or less. A fragrance was added to the mixture after the mixture was cooled to 45° C. or less. Then, the mixture was uniformly stirred. The mixture was cooled to room temperature. Then, the moisture content vaporized by heating was supplemented, and further stirring was performed for 30 minutes or more. The obtained hair shampoo was evaluated in accordance with the evaluation method.

| (Component) | (% by mass) |
|---|---|
| Sodium internal olefin sulfonate (3) | 10.0 |
| Sodium internal olefin sulfonate (4) | 2.5 |
| Polyoxyethylene (1) lauryletherammonium sulfate *1 | 2.0 |
| Lauric acid monoethanolamide | 0.8 |
| Ethylene glycol distearate *2 | 1.0 |
| Silicone *3 | 1.0 |
| Fragrance, methylparaben | q.s. |
| Purified water | Balance |
| Total | 100.0 |

*1: made by Kao Corporation, 2.9% of EMAL 170S-A (effective component of 70%) was added

*2: made by Cognis GmbH, 5% of Euperlan PK-810 (effective component of 20%) was added

*3: made by Dow Corning Toray Co., Ltd., 1.82% of silicone BY22-050A (effective component of 55%) was added The hair shampoo had excellent rinse feel, good combability after rinsing and softness of hair, and feel of use having excellent manageability after drying and durability of foam.

Example 128 (Facial Cleanser)

A facial cleanser having the composition below was produced in the same manner as in Example 127, and was evaluated. The facial cleanser had excellent rinse feel, and feel of use having excellent moist feeling after towel dry and durability of foam.

| (Component) | (% by mass) |
|---|---|
| Sodium internal olefin sulfonate (4) | 15.0 |
| Palm oil fatty acid monoethanolamide | 2.0 |
| Highly polymerized dimethylsiloxane *1 | 3.0 |
| Cocoamido propylbetaine | 5.0 |
| pH adjuster | q.s. |
| Purified water | Balance |
| Total | 100.0 |

*1: made by Dow Corning Toray Co., Ltd., trade name; BY22-060 (effective component of 60%)

INDUSTRIAL APPLICABILITY

The cleansing composition of the present invention can be favorably used in the fields of hair shampoo, body shampoo, facial cleanser, makeup remover, and hand soap, and the like, and further, it is also favorably applicable to animals such as dogs and cats.

The invention claimed is:

1. A cleansing composition for skin or hair comprising an internal olefin sulfonate (A) having 12 or more and 24 or less carbon atoms, wherein a total content of an internal olefin sulfonate having 16 carbon atoms and an internal olefin sulfonate having 18 carbon atoms in the internal olefin sulfonate (A) is 95% by mass or more;

a content of an internal olefin sulfonate in which a sulfonate group is present at the C-2 position in the internal olefin sulfonate (A) is 25% to 5% by mass; and a mass content ratio of a hydroxy form of the internal olefin sulfonate to an olefin form of the internal olefin sulfonate in the internal olefin sulfonate (A) (hydroxyl form/olefin form) is from 80/20 to 100/0.

2. The cleansing composition for skin or hair according to claim 1, wherein the number of carbon atoms in the internal olefin sulfonate (A) is 16 or more and 18 or less.

3. The cleansing composition for skin or hair according to claim 1, wherein a content of an internal olefin sulfonate in which a sulfonate group is present at a C-2 position in the internal olefin sulfonate (A) is less than 20% by mass.

4. The cleansing composition for skin or hair according to claim 1, wherein the internal olefin sulfonate (A) is obtained by sulfonating a raw material internal olefin having 12 or more and 24 or less carbon atoms, followed by neutralization and then hydrolysis.

5. The cleansing composition for skin or hair according to claim 1, further comprising a surfactant other than the internal olefin sulfonate (A).

6. The cleansing composition for skin or hair according to claim 1, further comprising a moisturizing agent.

7. The cleansing composition for skin or hair according to claim 1, further comprising an antibacterial agent or an anti-dandruff agent.

8. The cleansing composition for skin or hair according to claim 1, further comprising a pearling agent.

9. The cleansing composition for skin or hair according to claim 1, further comprising a fragrance.

10. The cleansing composition for skin or hair according to claim 1, further comprising an organic solvent.

11. The cleansing composition for skin or hair according to claim 1, further comprising a vitamin agent.

12. The cleansing composition for skin or hair according to claim 1, further comprising a thickener.

13. The cleansing composition for skin or hair according to claim 1, further comprising a water-soluble salt.

14. The cleansing composition for skin or hair according to claim 1, further comprising a chelating agent.

15. The cleansing composition for skin or hair according to claim 1, further comprising an oil solution.

16. The cleansing composition for skin or hair according to claim 1, further comprising an amphoteric polymer or a cationic polymer.

* * * * *